US007226948B2

(12) United States Patent
Pasinetti et al.

(10) Patent No.: US 7,226,948 B2
(45) Date of Patent: *Jun. 5, 2007

(54) TREATMENT OF NEURODEGENERATIVE CONDITIONS WITH NIMESULIDE

(75) Inventors: Giulio M. Pasinetti, New York, NY (US); Paul S. Aisen, Potomac, MD (US)

(73) Assignee: University of Mount Sinai School of Medicine of the City of New York, New York, NY (US)

( * ) Notice: Subject to any disclaimer, the term of this patent is extended or adjusted under 35 U.S.C. 154(b) by 764 days.

This patent is subject to a terminal disclaimer.

(21) Appl. No.: 10/150,461

(22) Filed: May 17, 2002

(65) Prior Publication Data

US 2006/0059576 A1 Mar. 16, 2006

Related U.S. Application Data

(60) Division of application No. 09/308,424, filed as application No. PCT/US97/21484 on Nov. 19, 1997, now Pat. No. 6,649,811, which is a continuation-in-part of application No. 08/831,402, filed on Apr. 1, 1997, now Pat. No. 5,985,930.

(60) Provisional application No. 60/033,332, filed on Nov. 21, 1996.

(51) Int. Cl.
*A01N 41/12* (2006.01)
*A61K 31/16* (2006.01)

(52) U.S. Cl. .................................... 514/607
(58) Field of Classification Search ............... 514/607
See application file for complete search history.

(56) References Cited

U.S. PATENT DOCUMENTS

| | | | | |
|---|---|---|---|---|
| 5,486,534 A | 1/1996 | Lee et al. | ........... | 514/406 |
| 5,510,361 A | 4/1996 | Scherz et al. | ........... | 514/378 |
| 5,510,368 A | 4/1996 | Lau et al. | ........... | 514/419 |
| 5,545,656 A | 8/1996 | Loose et al. | ........... | 514/414 |
| 5,547,975 A | 8/1996 | Talley et al. | ........... | 514/406 |
| 5,604,260 A | 2/1997 | Guay et al. | ........... | 514/605 |
| 5,753,694 A | 5/1998 | Shank | | |
| 5,985,930 A * | 11/1999 | Pasinetti et al. | ........... | 514/607 |
| 2002/0162130 A1 | 10/2002 | Pasinetti et al. | | |

FOREIGN PATENT DOCUMENTS

| | | |
|---|---|---|
| CA | 2164559 | 6/1996 |
| IT | 3002356 | 11/1996 |
| WO | WO 9413635 | 6/1994 |
| WO | WO 9414977 | 7/1994 |
| WO | WO 9500501 | 1/1995 |
| WO | WO 9603396 | 2/1996 |
| WO | WO 9607651 | 3/1996 |
| WO | WO 9608482 | 3/1996 |
| WO | WO 9611676 | 4/1996 |
| WO | WO 9616934 | 6/1996 |
| WO | WO 9619469 | 6/1996 |
| WO | WO 9623786 | 8/1996 |
| WO | WO 9625405 | 8/1996 |
| WO | WO 9820864 | 5/1998 |

OTHER PUBLICATIONS

Gouras, GK (2001) Current theories for the molecular and cellular pathogenesis of Alzheimer's disease. Expert Reviews in Molecular Medicine, May 31, http://www-ermm.cbcu.cam.ac.uk/01003167h.htm.*
Kumar et al. (1992) Basic Pathology, Fifth Edition, W.B. Saunders Company, Philadelphia, pp. 725-729.*
Price et al. (1998) Genetic neurodegenerative diseases: the human illness and transgenic models. Science 282: 1079-1083.*
Selkoe, DJ (2001) Alzheimer's disease: Genes, proteins, and therapy. Physiological Reviews 81(2): 741-766.*
Xavier Rabasseda: "Nimesulide: A selective cyclooxygenase 2 inhibitor anti-inflammatory drug" Drugs of Today, vol. 32, No. 5, Jul. 1996, pp. 365-384, XP002059316.
G. Tocco et al.: Cyclooxygenase-2 (COX-2) a developmentally regulated gene that shows regiona induction to excitotoxic lesions in the rat brain Society for Neuroscience Abstracts, p. 216 XP002059317.
M. Nakayama et al.; "The immediate early gene cyclooxygenase-2 is expressed in CA 1 neurons destined for apoptotic death following global ischemia" Society for Neuroscience Abstracts, vol. 21, No. 1-3, 1995, p. 1268 XP002059318.
M. Nakayama et al.: "Cyclooxygenase-2 promotes neuronal cell death after global ischenia in rat CA1 hippocampus" Society for Neuroscience Abstracts, vol. 22, No. 1-3, 1996, p. 1670 XP002059319.
Raymund L. Zhu et al.: "Cyclooxygenase-2 is expressed in vulnerable neurons in the rat brain by kainate excitotoxicity" Society for Neuroscience Abstracts, vol. 21, No.1-3, 1995, p. 300 XP002059320.
Tianxing, Yang et al.: "Tissue-specificity of cyclooxygenase-2 promoter in transgenic mice" Journal of the American Society of Nephrology, vol. 7, No. 9, 1996, p. 1652 XP002071234.
IBC's Industry Symposium on COS-2 Inhibitors, Aug. 6-7, 1998, San Diego, CA, abstract by D Pasinetti.
Mattson, 1998, "Experimental Models of Alzheimer's Disease" Science & Medicine Mar./Apr. 16-25.
McGeer and McGeer, 1998, "Inflammation and Alzheimer's Disease Potential Use of Anti-Inflammatory Agents" Neurol. Rev. 1(Suppl.):8-11.
Needleman and Isakson, 1998, "Selective Inhibition of Cyclooxygenase 2" Science & Medicine Jan./Feb.:26-35.

(Continued)

*Primary Examiner*—Anne-Marie Falk
(74) *Attorney, Agent, or Firm*—Baker Botts LLP

(57) ABSTRACT

The present invention relates to the use of nimesulide and structurally related compounds in the prevention and/or treatment of neurodegenerative conditions. It is based, at least in part, on the discovery that nimesulide exhibits a neuroprotective effect against β-amyloid induced cell death. Without being bound to any particular theory, it appears that nimesulide inhibits a non-inflammatory mechanism of neurodegeneration.

3 Claims, 32 Drawing Sheets

OTHER PUBLICATIONS

Figure 1:
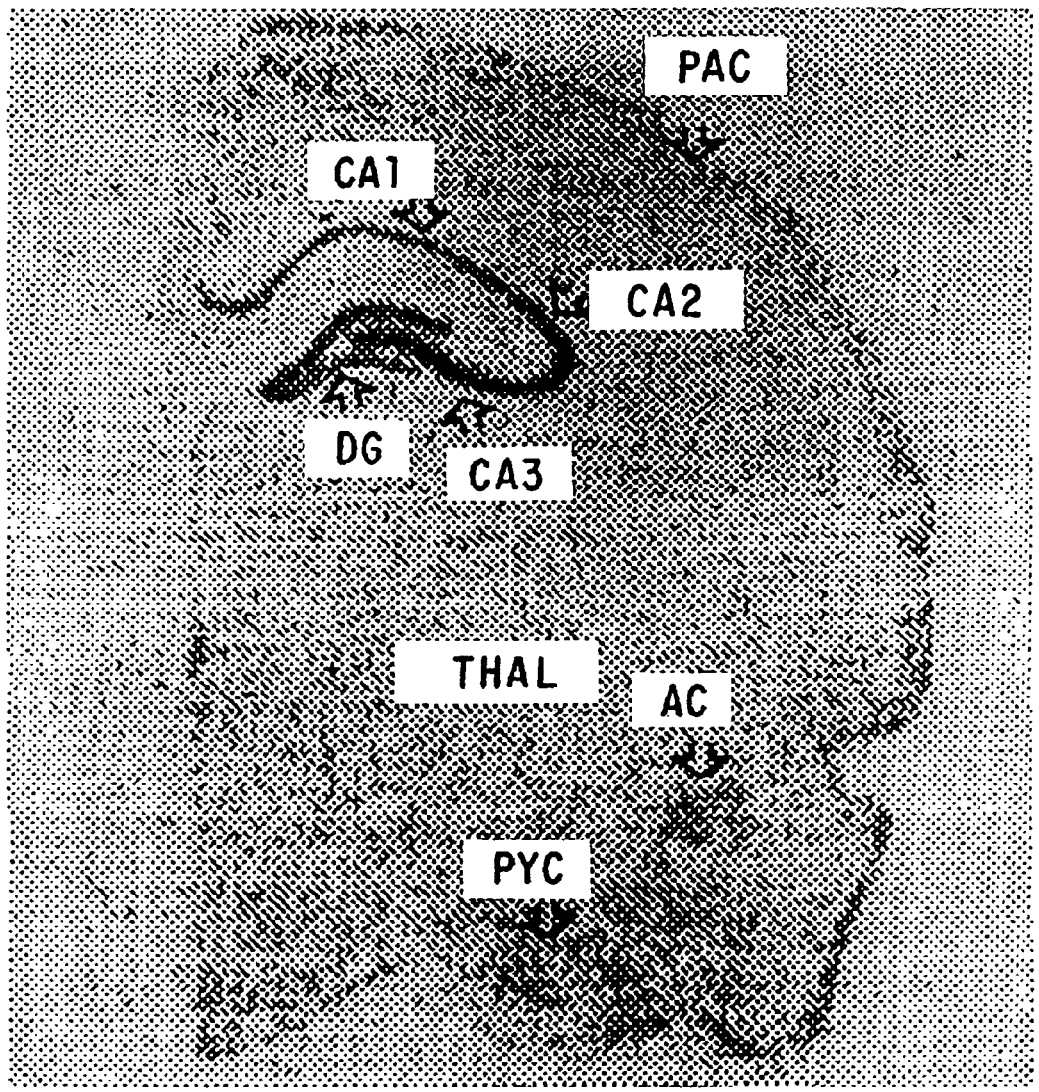

Lukiw and Bazan, 1997, "Cyclooxygenase-2 (COX2) RNA Message Stability in Alzheimer's Disease (AD) Neocortex" Soc. for Neurosci. Abstracts 23:2171.

Lukiw and Bazan, 1997, "Cyclooxygenase 2 RNA Message Abundance, Stability, and Hyperbariability in Sporadic alzheimer Neocortex" J. Neurosci. Res. 50:937-945.

Lundberg et al., 1997, "Nitric Oxide and Inflammation: The Answer is Blowing in the Wind" Nature Med. 3:30-31.

Crowe et al., 1997, "Apoptosis and Delayed Degeneration After Spinal Cord Injury in Rats and Monkeys" Nature Med. 3:73-76.

Adams et al., 1996, "Cycloogenase-2 Induction in Cerebral Cortex: An Intracellular Response to Synaptic Excitation" J. Neurochem. 66:6-13.

Aisen et al., 1996, "A Pilot Study of Prednisone in Alzheimer's Disease" Dementia 7:201-206.

Anderson et al., 1996, "DNA Damage and Apoptosis in Alzheimer's Disease: Colocalization with c-Jun Immunoreactivity, Relationship to Brain Area, and Effect of Postmortem Delay" The Journal of Neuroscience 16(5):1710-1719.

Chang et al., 1996, "Prostaglandin G/H Synthase-2 (Cyclooxygenase-2) mRNA Expression is Decreased in Alzheimer's Disease" Neurobiology of Aging (17)5:801-808.

Fagarasan and Aisen, 1996, "IL-1 and Anti-Inflammatory Drugs Modulate A β cytotoxicity in PC12 cells" Brain Res. 723:231-234.

Li et al., 1996, "β-Amyloid Induces Apoptosis in Human-Derived Neurotypic SH-SY5Y Cells" Brain Research 738:196-204.

McGreer et al., 1996, "Arthritis and Anti-inflammatory Agents as Possible Protective Factors for Alzheimer's Disease:" Neurology 47:425-432.

Kaufman et al., 1996, Cox-2 "A Synaptically Induced Enzyme, is Expressed by Excitatory Neurons at Postsynaptic Sites in Rat Cerebral Cortex" Proc. Natl. Acad. U.S.A. 93:2317.

Graham et al., 1996, "Cyclooxygenase 2 is Induced in Rat Brain After Kainate Induced Seizures and Promotes Neuronal Death in CA3 Hippocampus" Soc. for Neuroscience 22:Abstr. 818.15.

Pasinetti et al., 1996, "Inflammatory Mechanisms in Neurodegeneration and Alzheimer's Disease The Role of the Complement System" Neurobiology of Aging 17(5):707-716.

Tocco et al., 1996, Soc. for Neurosci. Abstracts 22:215 (citation in previous IDS incomplete).

Yang et al., 1996, "Tissue-Specificity of Cyclooxygenase-2 Promoter in Transgenic Mice" ,J. Am. Soc. Nephrol. 7:1652. (Abstract only;citation in previous IDS inaccurately listed first name o inventor).

Aisen, 1995, "Anti-Inflammatory Therapy for Alzheimer's Disease" Dementia 9(2):173-182.

Anderson et al., 1995, "Differential Induction of Immediate Early Gene Protein in Cultured Neurons by β-Amyloid (Aβ): Association of c-Jun with Aβ-Induced Apoptosis" Journal of Neurochemistry 65(4):1487-1498.

Oda et al., 1995, "Complement and β-amyloid (Aβ) Neurotoxicity in vitro: A Model for Alzheimer's Disease" Alzheimer's Research 1:29-34.

Smale et al., 1995, "Evidence for Apoptotic Cell Death in Alzheimer's Disease" Exp. Neurol. 133:225-230.

Tsujii and DuBois, 1995, "Alterations in Cellular Adhesion and Apoptosis in Epithelial Cells Overexpressing Prostaglandin Endoperoxide Synthase 2" Cell 83:493-501.

Aisen and Davis, 1994, "Inflammatory Mechanisms in Alzheimer's Disease: Implications for Therapy" Am J. Psychiatry 151(8):1105-1113.

Anderson et al., 1994, "Increased Immunoreactivity for Jun-and Fos-Related Proteins in Alzheimer's Disease: Association with Pathology" Experimental Neurology 125:286-295.

Loo et al., 1993, "Apoptosis is Induced by β-Amyloid in Cultured Central Nervous System Neurons" Proc. Natl. Acad. Sci. USA 90:1-5.

Rogers et al., 1993, "Clinical Trial of Indomethacin in Alzheimer's Disease" Neurology 43:1609-1611.

Yamagata, 1993, "Expression of a Mitogen-Inducible Cyclooxygenase in Brain neurons: Regulation by Synaptic Activity and Glucocorticoids" Neuron 11:371-386.

Bannwarth et al., 1989, "Clinical Pharmacokinetics of Nonsteroidal Anti-inflammatory Drugs in the Cerebrospinal Fluid" Biomed. & Pharmacother 43:121-126.

Murphy et al., 1989, "Glutamate Toxicity in a Neuronal Cell Line Involves Inhibition of Cystine Transport Leading to Oxidative Stress" Neuron 2:1547-1558.

Merck Index, p. 1125, No. 6640 Nimesulide.

Aisen et al., Randomized pilot study of treatment in Alzheimer's disease, Neurology, 2002, vol. 58, No. 7, pp. 1050-1054.

Cernak et al., Activation of cyclo-oxygenase-2 contributes to motor and cognitive dysfunction following diffuse traumatic brain injury in rats, *Clinical and Experimental pharmacology and Physiology*, 2001, vol. 28, pp. 922-925.

* cited by examiner

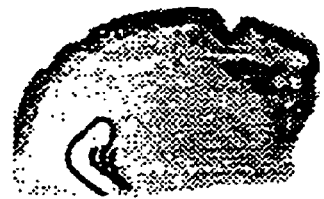
FIG. 3

 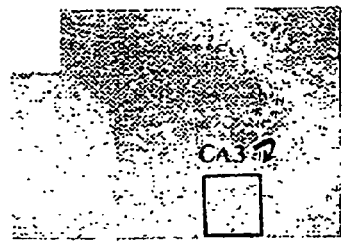 
FIG.7A  FIG.7B  FIG.7C
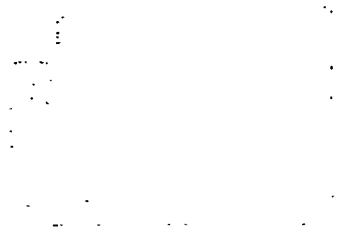  
FIG.7D  FIG.7E  FIG.7F
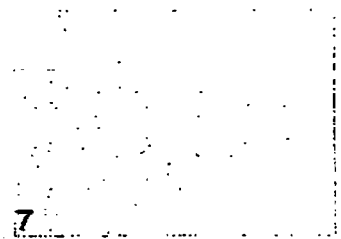 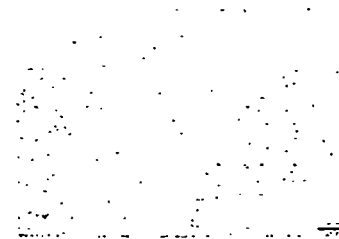 
FIG.7G  FIG.7H  FIG.7I

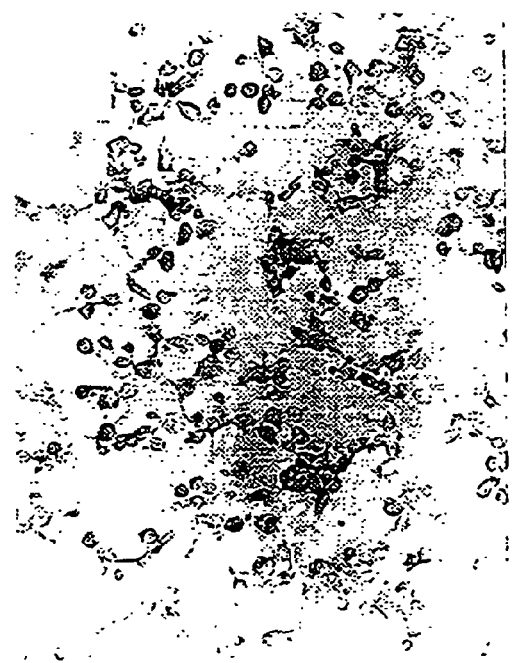
FIG.8A  FIG.8B
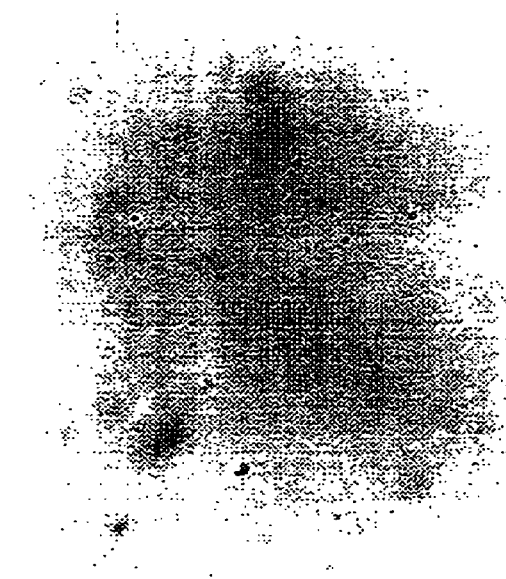
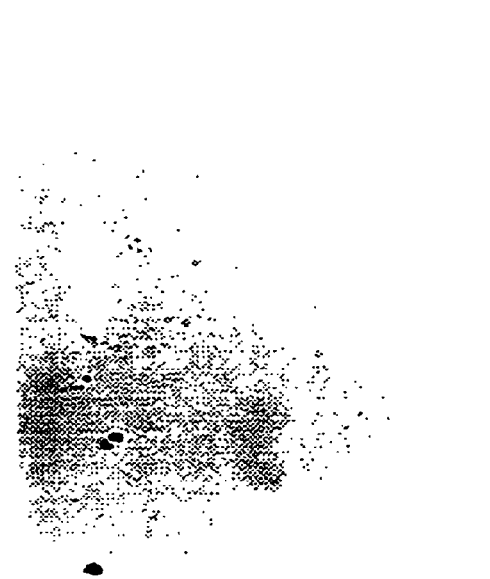
FIG.8C  FIG.8D

FIG.11B
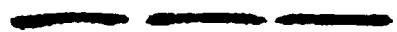
Actin
FIG.11D

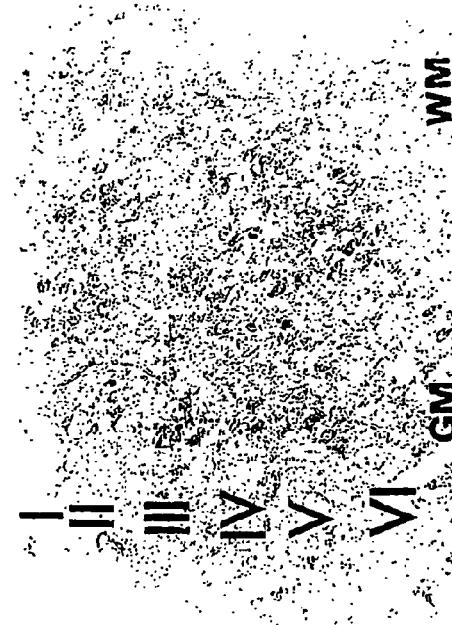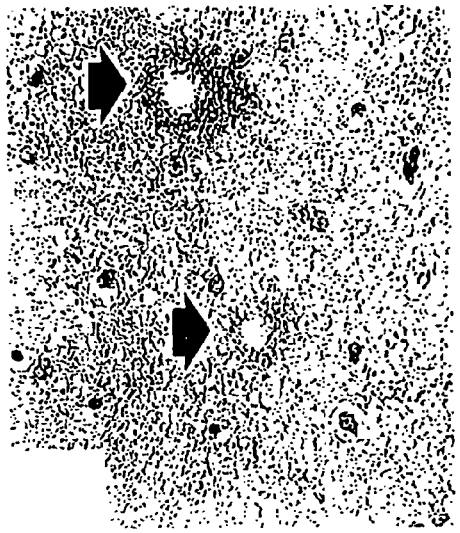

FIG. 15A

TgNHC32

WILD

TREATMENT OF NEURODEGENERATIVE CONDITIONS WITH NIMESULIDE

CROSS REFERENCE TO RELATED APPLICATIONS

This application is a divisional of U.S. patent application No. 09/308,424, filed on Jul. 16, 1999, now U.S. Pat. No. 6,649,811 which is a United States national stage application based on International Patent Application No. PCT/US97/21484, filed Nov. 19, 1997, which is a continuation-in-part of U.S. patent application Ser. No. 08/831,402, filed Apr. 1, 1997, now U.S. Pat. No. 5,985,930, and which claims priority to U.S. Provisional Application No. 60/033,332, filed Nov. 21, 1996.

1. INTRODUCTION

The present invention relates to the use of nimesulide and structurally related compounds in the prevention and/or treatment of neurodegenerative conditions such as Alzheimer's Disease. It is based, at least in part, on the discovery that nimesulide, in effective concentrations, inhibits cell death.

2. BACKGROUND OF THE INVENTION

2.1. Alzheimer's Disease

Sporadic Alzheimer's Disease is the major neurodegenerative disease associated with aging, the risk of developing the disease rising exponentially between the ages of 65 and 85, doubling every five years. Histologically, the hallmarks of Alzheimer's Disease are the deposition of amyloid in senile plaques and in the walls of cerebral blood vessels; the presence of neurofibrillary tangles, and neurodegeneration. The etiology of Alzheimer's Disease, however, is not well understood. Genetic factors have been proposed to play a role, including trisomy 21, mutations in the amyloid β-protein precursor ("APP") gene, the presenilin-1 (PS1) and presenilin-2 (PS2) genes, and the presence of the apolipoprotein E type 4 allele (Younkin, 1995, Ann. Neurol. 37:287-288; Lendon et al., 1997, JAMA A 277:825). Several studies have indicated that β-amyloid induces apoptosis in cultured neurons (Loo et al., 1993, Proc. Natl. Acad. Sci. U.S.A. 90:7951-7955; Li et al., 1996, Brain Res. 738:196-204). Such induction may involve the immediate early gene proteins, c-jun and fos (Anderson et al., 1995, J. Neurochemistry 65:1487-1498; Anderson et al., 1994, Experimental Neurology 125:286-295; Anderson et al., 1996, J. Neurosci. 16:1710-1719).

It has been proposed that apoptosis may be involved in the pathogenesis of Alzheimer's disease (Smale et al., 1995, Exp. Neurol. 133:225-230; Anderson et al., 1996,J. Neurosci. 16:1710-1719; Anderson et al., 1994, Exp. Neurol. 125:286-295). Inflammatory mechanisms have also been implicated; (Pasinetti, 1996, Neurobiol. Ageing 17:707-716) supportive of such a mechanism are the observations that acute phase proteins are elevated in the serum of Alzheimer's Disease patients, and are deposited in amyloid plaques; activated microglial cells tend to localize in the vicinity of senile plaques, and complement components have been localized around dystrophic neurites and neurofibrillary tangles (Aisen and Davis, 1994, Am. J. Psychiatry 151:1105-1113). Anti inflammatory agents have been suggested as potential therapeutic agents (Aisen et al., 1996, Dementia 7:201-206; McGeer et al., 1996, Neurology 47:425-432). Because they tend to have fewer adverse side effects, selective inhibitors of the enzyme cyclooxygenase-2 have been advanced as agents for treating such inflammation (International Publication No. WO 94/13635 by Merck Frosst Canada Inc.). Prior to the present invention, however, it had not been believed that such agents could be used to inhibit non-inflammatory aspects of neurodegeneration in the context of Alzheimer's Disease or otherwise.

2.2. Cyclooxygenase-2

Cyclooxygenases ("COXs") are enzymes that catalyze the formation of prostaglandin ("PG")-$H_2$ from arachidonic acid (AA). PG-$H_2$ is further metabolized to physiologically active PGs (e.g., PG-$D_2$, PG-$E_2$ and PG-$F_{2\alpha}$), prostacyclin (PG-$I_2$) and thromboxanes. Specific PGs have diverse, often antagonistic effects on different tissues. For example, PG-$I_2$ and PG-$E_2$ are potent vasodilators that may contribute to the inflammatory response, whereas PG-$F_{2\alpha}$ is a vasoconstrictor.

There are two known COX isoforms, COX-1 and COX-2, which, though physiologically distinct, are similar in amino acid sequence and enzymatic functions. COX-1 is constitutively expressed at different levels in different cell types. COX-2, however, is not constitutively expressed, and is generally undetectable in normal peripheral tissues (Kujubu et al., 1991, J. Biol. Chem. 266:12866-12872; O'Banion et al. 1992, Proc. Natl. Acad. Sci. U.S.A. 89:4888-4892). Rather, COX-2 expression is inducible (for example, by mitogens) and COX-2 mRNA levels have been observed to rise rapidly in response to inflammatory stimuli such as interleukin-1β and lipopolysaccharide, and to decrease in response to glucocorticoids. When subjected to these same factors, COX-1 mRNA levels remain substantially unchanged, suggesting that COX-2 is the isoform which mediates inflammation (Cao et al., 1995, Brain Res. 697: 187-196; O'Banion et al. 1992, Proc. Natl. Acad. Sci. U.S.A. 89:4888-4892).

Recent evidence suggests that COX-2 may play a role in mechanisms of cell survival and cell adhesion in peripheral cells (Lu et al., 1996, Proc. Natl. Acad. Sci. U.S.A. 92:7961-7965; Tsujii et al., 1995, Cell 83:493-501). Tsuji et al. reports that epithelial cells engineered to express elevated levels of COX-2 were resistant to butyrate-induced apoptosis, exhibited elevated BCL2 protein expression, and reduced transforming growth factor β2 receptor levels (Tsuji et al., 1995, Cell 83:493-501). Lu et al. indicates that non-steroidal anti inflammatory drugs may induce an apoptotic mechanism involving the COX system.

The roles of COX-1, COX-2 and PG synthesis in normal brain, and in the context of Alzheimer's Disease, have not been fully characterized to date. The importance of PGs in brain physiology may be independent of inflammatory mechanisms. In the brain, PG receptors have been identified in the hypothalamus, thalamus, and limbic system (Watanabe et al., 1989, Brain Res. 478:143-148). PGs are involved in hypothalamic-pituitary hormone secretion (Kinoshita et al., 1982, Endocrinol. 110:2207-2209), regulation of temperature and the sleep-wake cycle (Hayaishi, 1988, J. Biol. Chem. 263:14593-14596). There is recent evidence that COX-2 mRNA is expressed and regulated in rat brain by synaptic activity and glucocorticoids (Adams et al., 1996, J. Neurochem. 66:6-13; Kaufmann et al., Proc. Natl. Acad. Sci. U.S.A. 93:2317-2321; Yamagata et al., 1993, Neuron 11:371-386). These studies indicate that COX-2 is regulated as an immediate early gene in the brain, and suggest that PGs may be important in trans-synaptic signaling and long-term potentiation. Chang et al. (1996, Neurobiol. of Aging 17:801-808) report that COX-2 mRNA expression is decreased in Alzheimer's disease.

3. SUMMARY OF THE INVENTION

The present invention relates to the use of nimesulide and structurally related compounds in the prevention and/or treatment of neurodegenerative conditions. It is based, at least in part, on the discoveries that (i) COX-2 expression in models of neurodegeneration is increased in neurons rather than glial cells (consistent with a non-inflammatory mechanism), and (ii) nimesulide exhibits a neuroprotective effect against β-amyloid induced neuronal cell death. This latter finding is particularly unexpected in view of the ability of COX-inhibitors to increase apoptosis of non-neuronal cells. Without being bound to any particular theory, it appears that nimesulide inhibits a non-inflammatory mechanism of neurodegeneration.

4. DESCRIPTION OF THE FIGURES

FIG. 1. Regional expression of COX-2 mRNA in control unlesioned male rat brain. COX-2 mRNA expression was assessed by in situ hybridization and visualized by X-ray autoradiography. Abbreviations: DG, dentate gyrus; CA1, CA2 and CA3 subregions of the neuronal pyramidal layer of the hippocampal formation; PAC, parietal cortex; PYC, pyriform cortex; AC, amygdaloid complex; THAL, ventroposterior thalamic nucleic. Adapted from plate 24 of Paxinos and Watson, 1986 (*The Rat Brain in Steriotaxic Coordinates*, Academic Press, NY).

Figure 2:
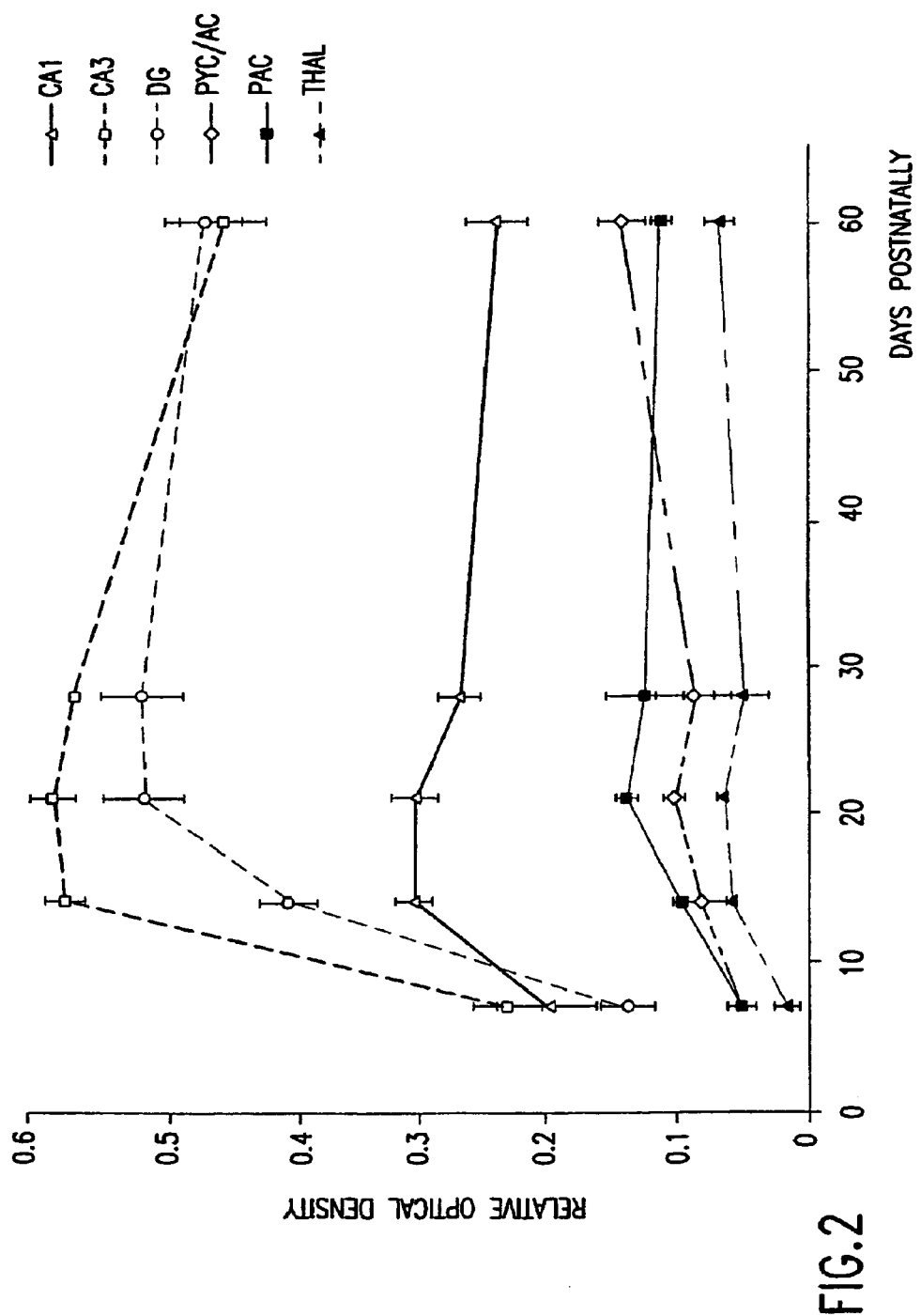

FIG. 2. Maturational regulation of COX-2 mRNA expression in rat brain. Optical densities were quantified from autoradiographic images. Abbreviations, as above and as follows: PYC/AC, pyriform and amygdaloid complex that were quantified for COX-2 mRNA expression as a single brain region. N=5-8 per time point.

FIG. 3. Maturational influence on COX-2 mRNA expression during response to KA-induced seizures. Micrographs were generated from autoradiographic images. For anatomical distribution of changes, refer to FIG. 1. Control, unlesioned vehicle-injected rats; KA 8 H, KA-treated rats 8 hours prior to sacrifice; postnatal days P-7, P-14, and P-21.

FIG. 4 A-D. Time course of COX-2 mRNA changes in rat brain during responses to KA treatment: maturational influences and regional distribution of changes. Optical densities were quantified from autoradiographic images. Data are expressed as means±SEM, N=4=6 per group. *$P<0.0$ vs 0 H group (saline injected group); 4 h, 8 h, 16 h, 30 h, 120 h, time in hours after onset of KA-induced seizures.

FIG. 5 A-D. Maturational influence on the distribution of COX-2 mRNA expression and induction in rat hippocampus. COX-2 mRNA in P21 (A,B) and adult (C,D) hippocampal formations as assessed by in situ hybridization assay and visualized by emulsion autoradiography using dark-field illumination. In A and C, COX-2 mRNA expression in control rats (vehicle injected); in B and D, COX-2 mRNA 8 hours after onset of KA-induced seizures. Arrows point toward the superficial layer of the DG (stratum granulosum). Scale bar=200 μm.

Figure 6:
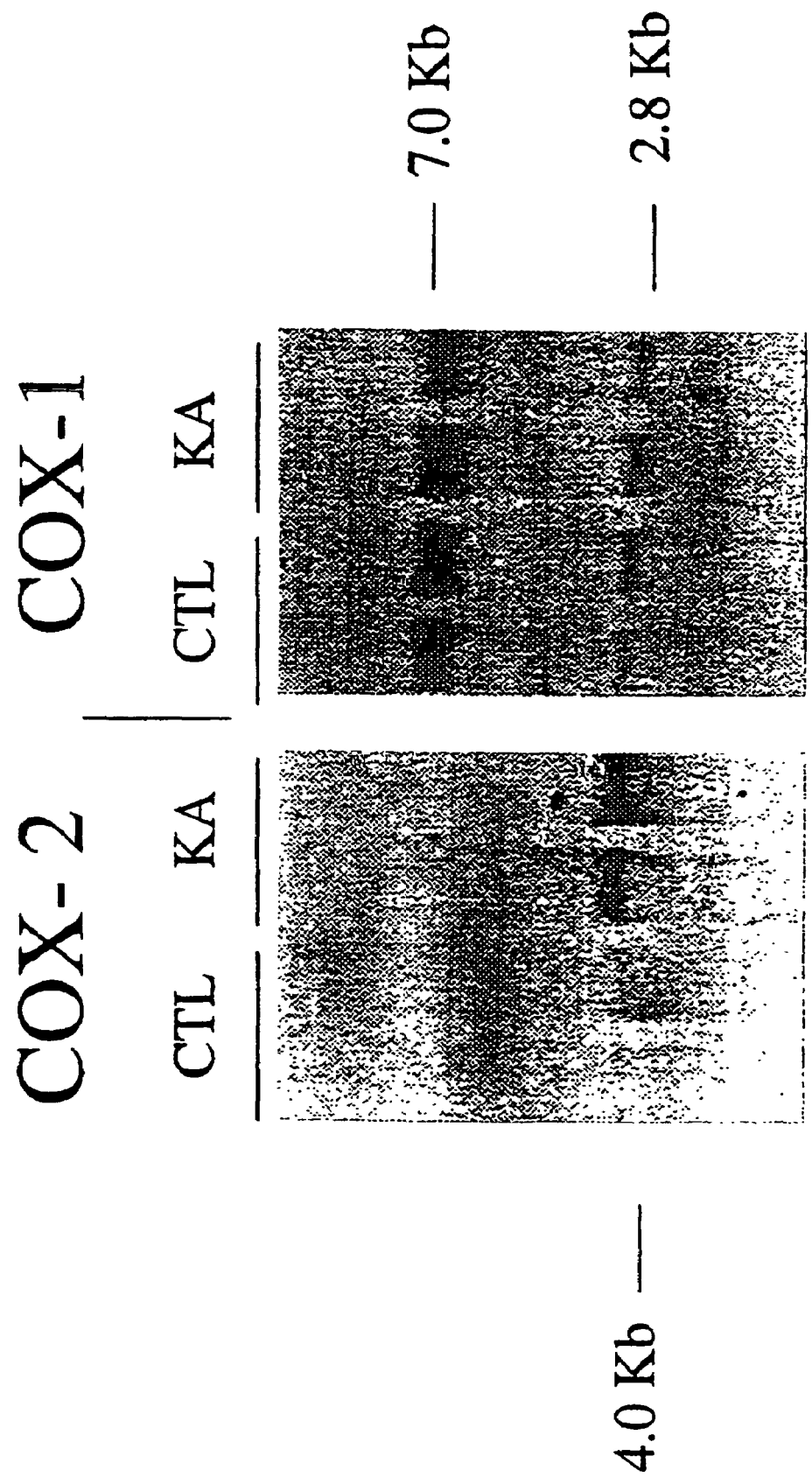

FIG. 6. Selective induction of hippocampal COX-2 but not COX-1 mRNAs during response to KA-induced seizures as assessed by gel blot hybridization assay. CTL, control saline-injected rats; KA, KA-treated rats 12 hours post lesioning.

FIG. 7 A-I. KA-induced COX-2 and apoptosis in adult rat brain. In (A,B), COX-2 mRNA expression in CA3 hippocampal pyramidal neurons of control and KA-treated rat, respectively; in (C), CA3 subregion of the hippocampal formation of KA-lesioned rats showing neurons with apoptotic features (arrows). In (D,E), COX-2 mRNA expression in pyriform cortex of control and KA-treated rat respectively. In (F), arrows point toward apoptotic cells of pyriform cortex of KA-lesioned rats. In (G,H), COX-2 mRNA expression in cells of the amygdaloid complex of control and KA-treated rats, respectively. In (I), arrows point toward apoptotic cells of the amygdaloid complex of KA-lesioned rats. COX-2 mRNA was assayed by in situ hybridization and visualized by emulsion autoradiography under dark field illumination. In situ 3' end-labeling was used to assess apoptotic features following KA treatment. Scale bar: in A,B,D,E,G, and H=200 μm; in C,F and I=40 μm.

FIG. 8 A-D. Immunocytochemical evidence of neuronal COX-2 expression/regulation in response to glutamate in vitro. COX-2-like immunoreactivity in monotypic cultures of rat primary hippocampal neurons in (A) control and (B) after glutamate exposure (12 hours). In (C,D) control and glutamate treated cultures immunoreacted with immunoadsorbed COX-2 antibody, respectively. Scale bar=50 μm.

FIG. 9 A-C. Effect of nimesulide on endotoxin-mediated synthesis/secretion of cytokines and nitrites in glia. The effect of $10^{-9}$ M nimesulide on the synthesis/secretion of (A) TNF, (B) NO intermediates (Griess reaction) and (C) $PGE_2$, as assessed in BV2 mouse immortalized microglial cells. Mean±SEM, n=8-10 per group. Lipopolysaccharide ("LPS")=5 μg/ml. LPS and nimesulide were added in combination to cultures; incubation time was 24 hours. Statistics used ANOVA, $p<0.05$.

FIG. 10 A-E. Time course of changes of COX-2 protein in P19 cells during response to conditions leading to apoptotic death. In (A), quantitative analysis of COX-2 induction in P19 cells, n=4-6 per group, $p<0.05$ vs. t=0. In (B), changes were assessed by western analysis, using chemiluminescent detection. In (C,D) the morphological appearance of apoptotic nuclei in P19 cells was assessed by Hoechst H33258 24 hours after serum removal (and replacement with N2 medium). In (E), the electrophoretic profile of DNA showing DNA laddering degradation was assessed 14 hours after serum removal (lane 1, control cells at t=0; lane 2, DNA laddering 14 hours after serum removal; lane 3, DNA markers). The COX-2 polyclonal antibody used in these studies was as described in Section 6. The COX-2 specific antibody recognizes two major bands having estimated molecular weights of about 70 and 65 kDa in total homogenates of mouse, rat and human brains.

FIG. 11A-E. Regulation of COX-2 during response to Aβ1-40 mediated oxidative stress in SH-SY5Y neuronal cells. (A) Bar graph showing the amount of COX-2 immunoreactivity present relative to control ("CTL"). The immunoreactivity measurement was derived from the data shown in (B). (B) Western blot of proteins prepared from control SH-SY5Y cells or cells exposed to Aβ peptides for 48 or 72 hours, reacted with COX-2 antisera. (C) Results of MTT assays of control or Aβ-treated SH-SY5Y cells. (D) The immunoblot shown in (B) stripped and immunoreacted with actin antisera (E) SH-SY5Y cultures were examined for apoptotic mechanisms.

Figure 12:
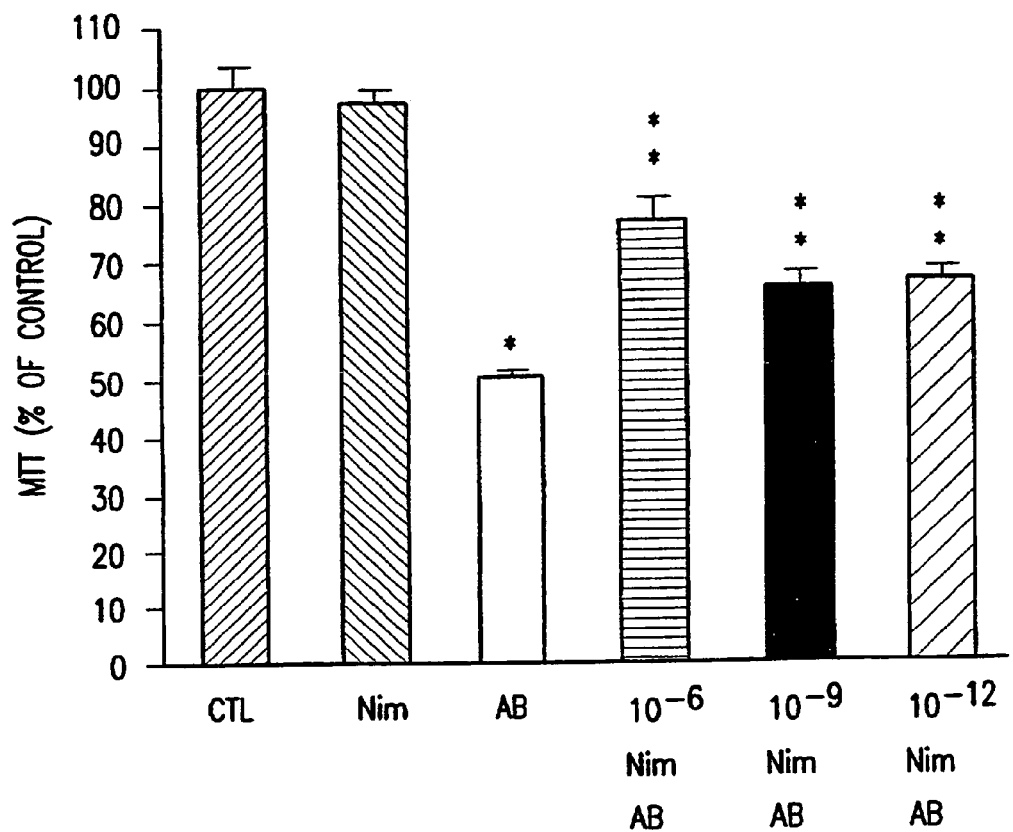

FIG. 12. Protective effect of nimesulide on Aβ1-40 mediated neurotoxicity as assessed by MTT assay using SH-SY5Y neuronal cells. Abbreviations: CTL control; NIM nimesulide; A B-β-amyloid (1-40). *$P<0.01$ vs CTL, **$P<0.05$ vs. CTL.

Figure 13:
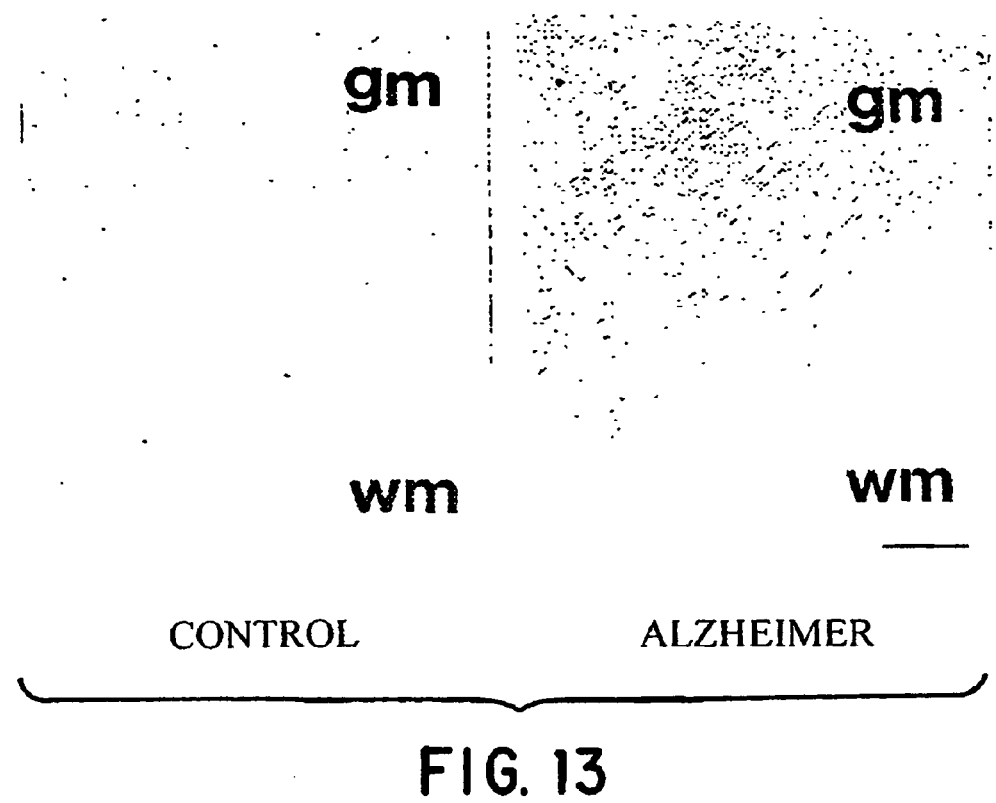

FIG. 13. Micrographs showing induction of COX-2 immunoreactivity in temporal cortex of AD and age-matched neurological controls. The micrographs show a selective induction of COX-2 immunostaining in neuron-rich grey matter ("gm") but not glia-rich white matter ("wm") regions.

FIG. 14 A-D. COX-2 immunostaining of neurons in frontal cortex of AD brain and co-localization of COX-2 immunostaining with AD plaques in frontal cortex of AD brains. In (A,B), immunostaining of COX-2 neurons of AD are shown (A, low power; B, high power magnification). In (C), immunostaining of diffuse plaques. In (D), COX-2 in neuritic plaques as assessed by Aβ immunostaining on adjacent tissue sections.

FIG. 15A-D. COX-2 expression in AD brain frontal cortex. (A) Northern blots of COX-2 and COX-1 mRNA in AD frontal cortex relative to controls quantitative analysis of data is in (B). (C) Western blots of COX-2 protein in AD frontal cortex and control; quantitative analysis of data is in (D).

Figure 16:
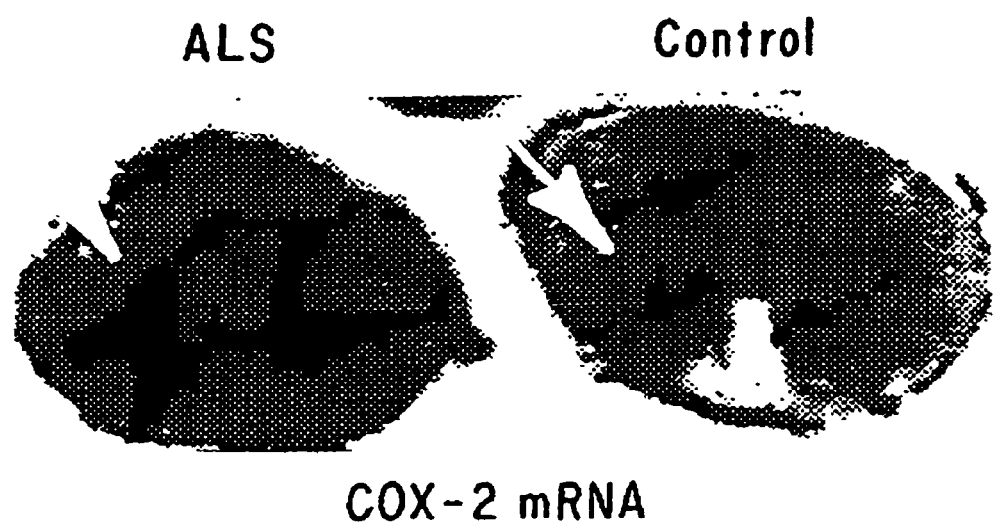
Figure 17A:
Figure 17B:
Figure 17C:
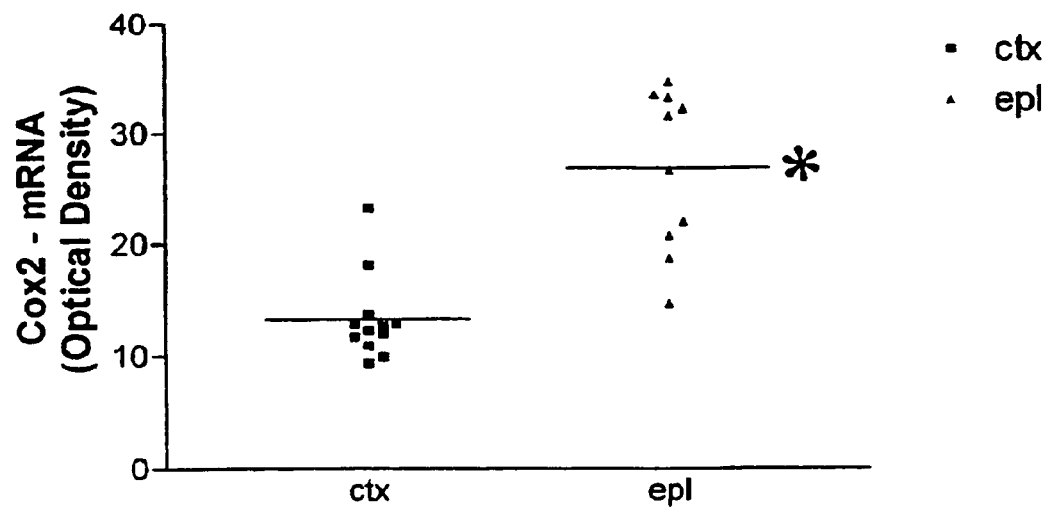
Figure 17D:
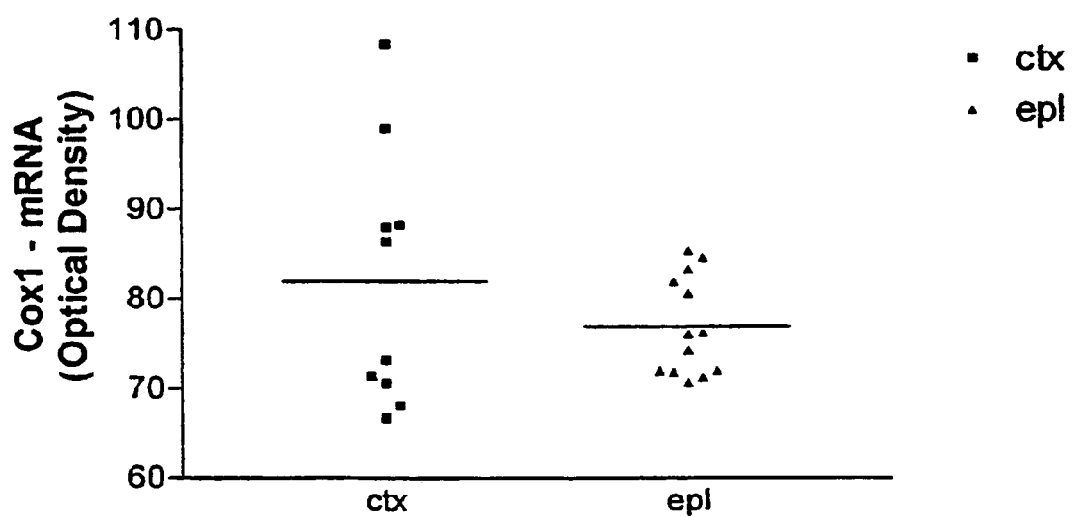

FIG. 16. COX-2 mRNA regulation in neurons of the anterior and posterior horn of the spinal cord of ALS and neurological controls. Autoradiographic images were visualized by X-ray film. The arrow pointed toward the ventral horn shows intense induction of COX-2 mRNA signal in the ALS case.

FIG. 17A-D. COX-2 mRNA elevation in a biopsy of human cortical epileptic foci as assessed by in situ hybridization assay. Autoradiographic images were visualized by X-ray film. Arrow pointed toward the cortical layers showing intense COX-2 mRNA signal in epileptic brain (A) versus control (B). Parts (C) and (D) show analysis of compiled data relating to COX-2 and COX-1 mRNA levels.

Figure 18:
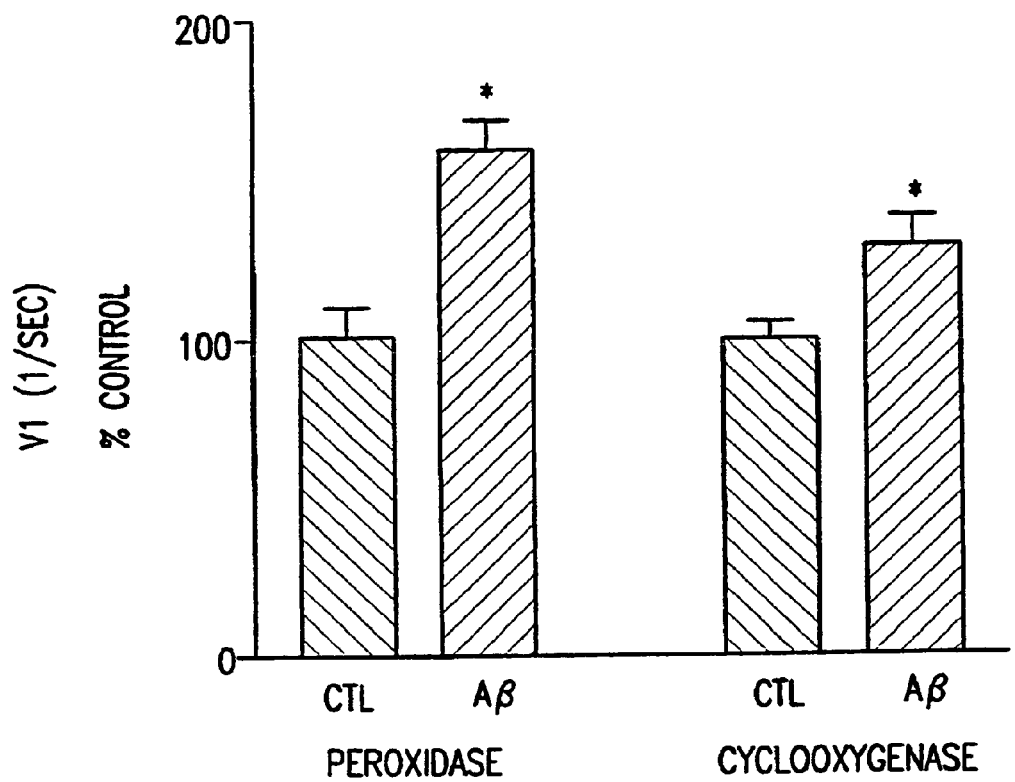

FIG. 18. Potentiation of cyclooxygenase and peroxidase activities by aggregated Aβ peptides.

Figure 19A:
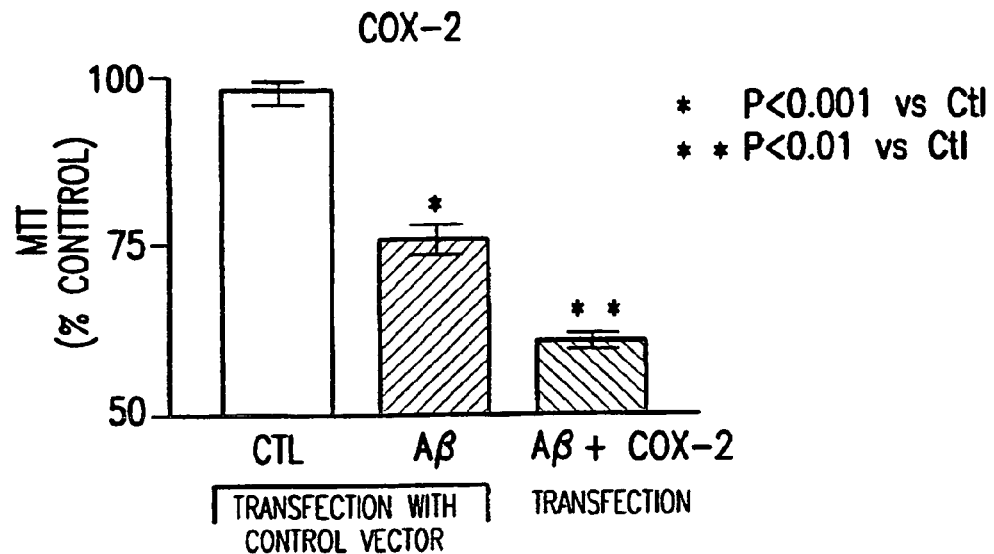
Figure 19B:
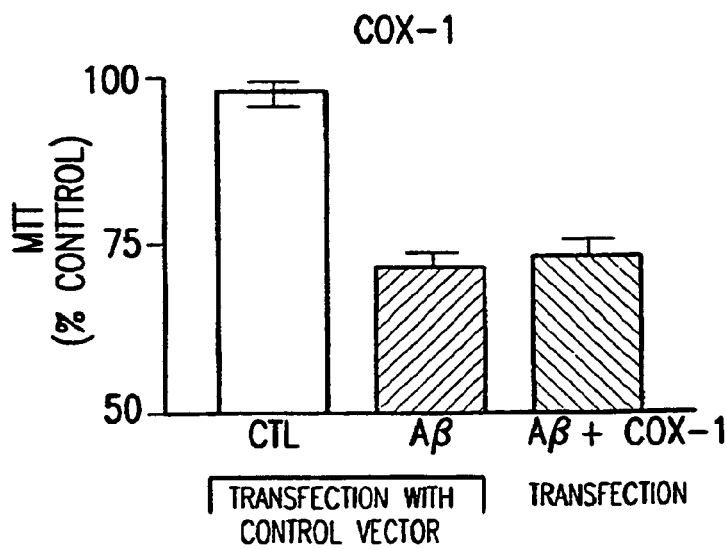

FIG. 19A-B. Transient expression of COX-2 in neuronal cells potentiates Aβ-mediated impairment of redox activity. SH-SY5Y neuronal cells were transfected with either the human COX-2 (A) or COX-1 (B) gene and treated with $A\beta_{25-35}$, and then redox activity was assessed by MTT assay.

Figure 20A:
Figure 20B:
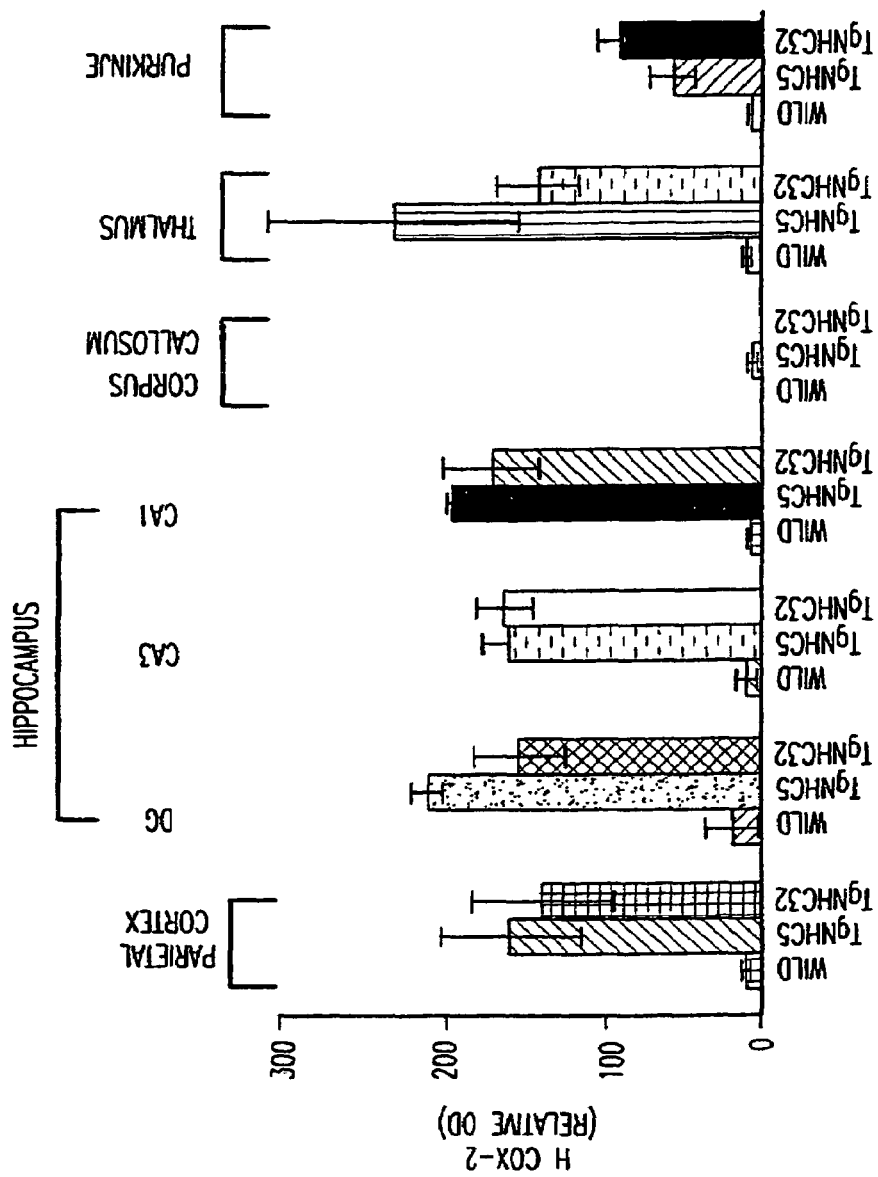

FIG. 20A-B. Generation of Transgenic Mice Expressing COX-2. (A) In situ hybridization demonstrates COX-2 mRNA expression in TgNHC32 mice but not wild-type (mice one month old). (B) Regional expression of hCOX-2 mRNA in NHC32 and NHC5 relative to wild-type, as quantified using Bioquant image-analysis.

Figure 21A:
Figure 21B:
Figure 21C:
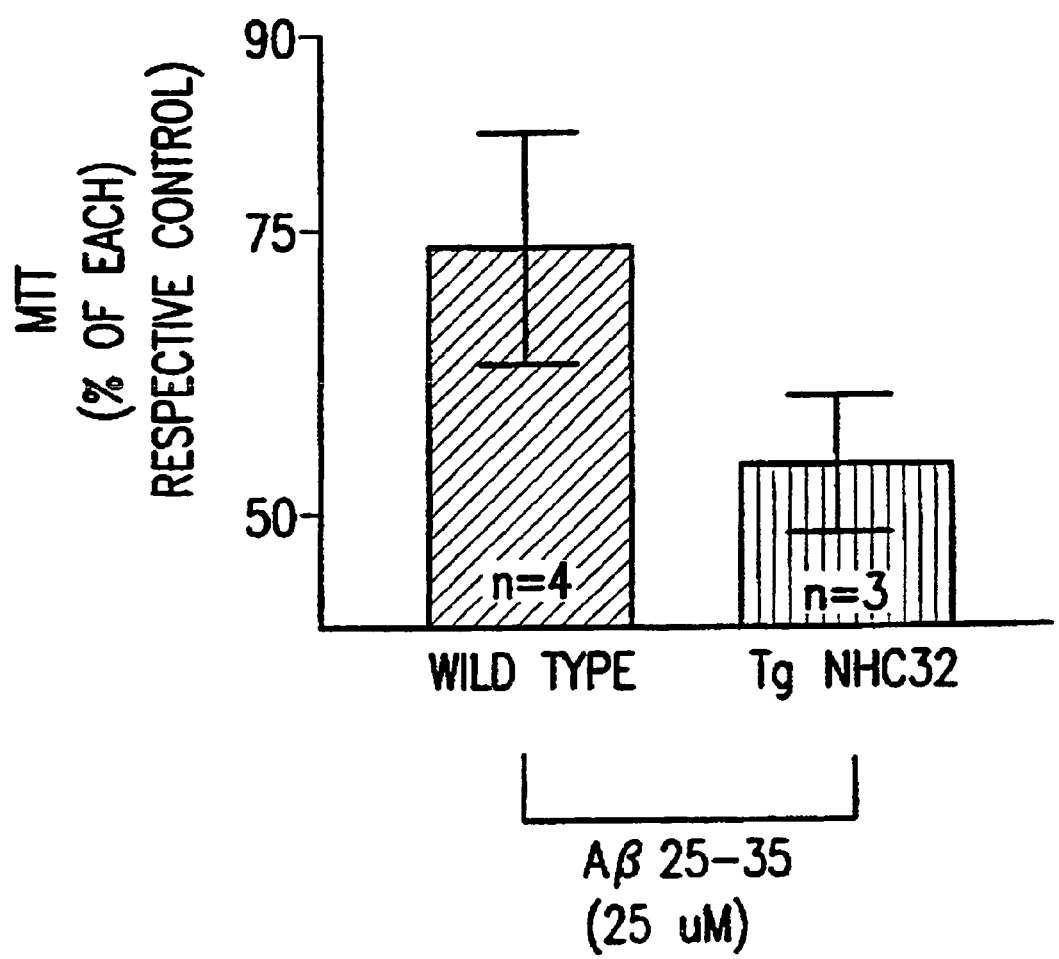

FIG. 21. hCOX-2 over-expression potentiates Aβ-mediated oxidative impairment in primary mouse neuronal cultures.

Figure 22A:
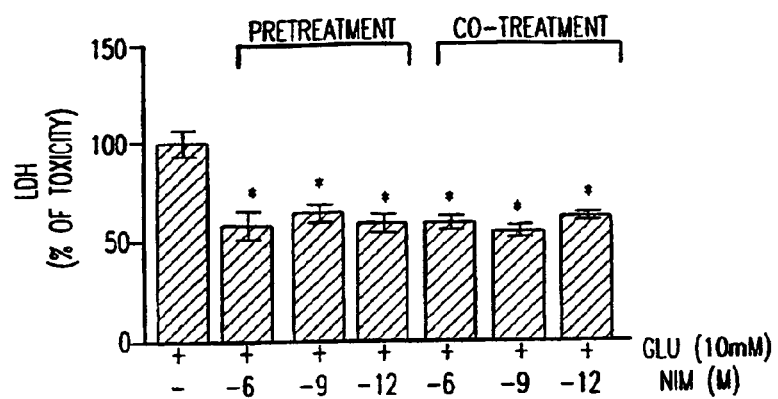
Figure 22B:
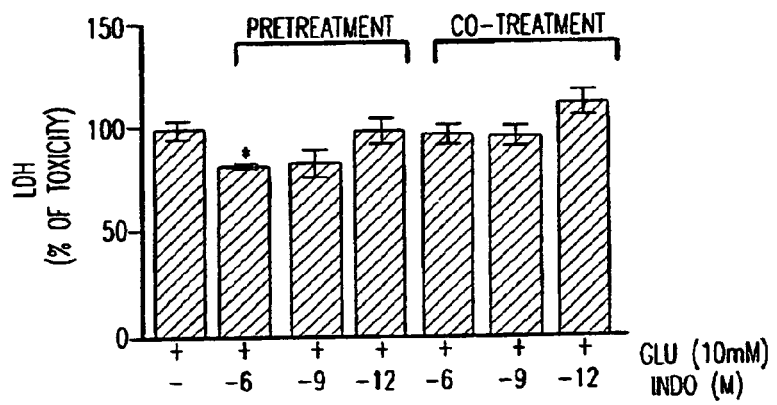
Figure 22C:
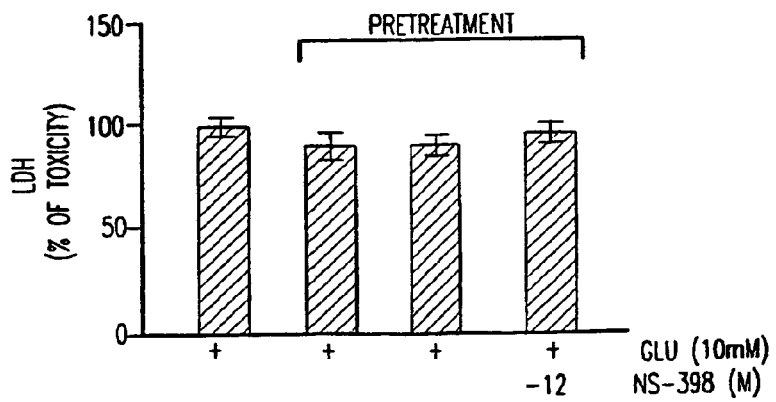

FIG. 22. Nimesulide protects B12 neuronal cells against glutamate mediated oxidative stress.

Figure 23A:
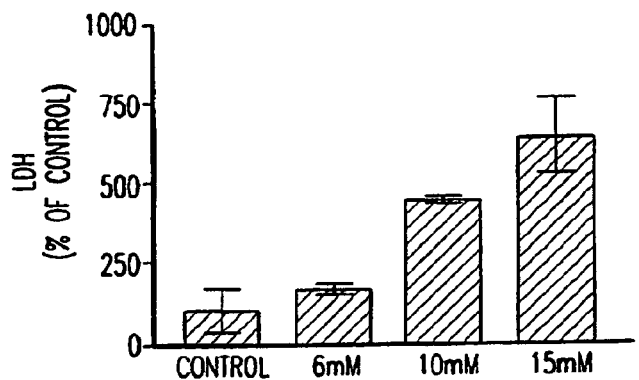
Figure 23B:
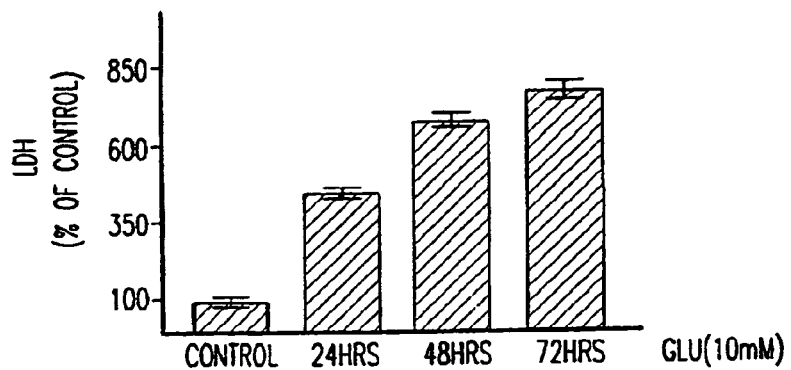
Figure 23C:
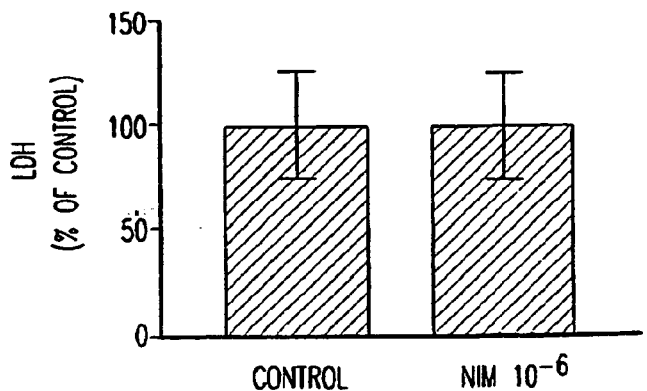

FIG. 23. Control studies for FIG. 22. Dose (A) and time course (B) association with glutamate mediated oxidative impairment as measured by LDH assay. (C) demonstrates lack of toxicity of nimesulide to B12 cultures.

5. DETAILED DESCRIPTION OF THE INVENTION

The present invention relates to the use of the cyclooxygenase-2 ("COX-2") selective inhibitor, nimesulide, and structurally related compounds in the prevention and/or treatment of neurodegenerative conditions. It is based, at least in part, on the discoveries that COX-2 expression increased in parallel with neuronal lesions produced by kainic acid and with induction of neuronal apoptosis in an established in vitro system (see Sections 6 and 8, below). Contrary to reports in the prior art that COX-2 plays a primary role in inflammation and may be involved in an inflammatory component of neurodegeneration (for example, in the context of Alzheimer's Disease), it has further been discovered that in the human brain, COX-2 expression appears to be restricted to neurons rather than to glial cells (whereas expression in glial cells would be expected if an inflammatory mechanism were operative: see Section 9, below). A correlation between COX-2 expression and the characteristic pathological change associated with Alzheimer's Disease, amyloid plaque, has been observed (see Section 9). Further, it has been demonstrated that nimesulide exerts a neuroprotective effect against β-amyloid induced cell death in neuronal cultures. In view of these findings, according to the invention, nimesulide and related compounds may be used to intervene in the process of apoptotic neuronal cell death associated with Alzheimer's Disease and other neurodegenerative conditions. Without being bound to any particular theory, the action of nimesulide and related compounds may be mediated by the reduction of the apoptotic effects of oxidative stress.

The term "nimesulide", as used herein, refers to a compound, 4nitro-2-phenoxymethanesulfonaninide, having a structure as set forth for Formula I below.

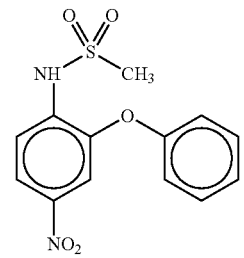

Compounds which are considered structurally related are compounds which have a similar bicyclic structure and which selectively inhibit COX-2. For example, substituents, analogs, and enantiomers of nimesulide are considered to be structurally related compounds. As a farther example, a structurally related compound may compete with nimesulide for binding to COX-2, or may bind to substantially the same location of COX-2, as determined crystallographically. Moreover, nimesulide, conjugated to another compound, is also considered to be a structurally related compound as defined herein.

Nimesulide, or a structurally related compound, may be administered so as to provide an effective concentration in the nervous system of the subject being treated. An effective concentration is defined herein as that concentration which inhibits neuronal cell death by at least 20 percent. In specific, nonlimiting embodiments of the invention, the concentration of nimesulide is at least 1 nanomolar, and preferably at least 1 micromolar in the location of neuronal cells which are desired to be treated. Desirably, the concentration of nimesulide is less than $10^{-3}$ molar to avoid toxicity. In one such specific embodiment, where the neurodegenerative condition to be treated is Alzheimer's Disease, the concentration of nimesulide in the hippocampal formation of the subject is at least 1 picomolar, preferably at least 1 nanomolar, and more preferably at least 1 micromolar. The corresponding serum concentrations may be at least 10 picomolar, preferably at least 10 nanomolar, and more preferably at least 10 micromolar. Equivalent amounts of structurally related compounds (adjusted to compensate for differences in potency) may also be used.

Nimesulide or a structurally related compound may be administered in any manner which achieves the desired effective concentration. For example, suitable routes of administration include oral, intravenous, subcutaneous, intramuscular, transdermal and intrathecal routes.

Nimesulide or a structurally related compound may be comprised in a suitable pharmaceutic carrier. Formulations may provide for sustained release.

For example, but not by way of limitation, nimesulide may be administered orally at doses of 2-800 mg/day, preferably 50-400 mg/day, and most preferably 200 mg/day.

Neurodegenerative conditions which may be treated according to the invention include, but are not limited to, Alzheimer's Disease, Parkinson's Disease, seizure-associated neurodegeneration, amyotrophic lateral sclerosis, spinal cord injury and other diseases wherein the condition is not conventionally regarded as an inflammation-mediated or autoimmune disorder.

6. EXAMPLE

Maturational Regulation and Regional Induction of Cyclooxygenase-2 in Rat Brain

6.1. Materials and Methods

Animals and Excitotoxic Lesions.

Male adult Sprague/Dawley rats of different ages were maintained in a controlled light and temperature environment, with food and water ad libidum. In adult rats (250-300 g), hippocampal excitotoxic lesions were induced by subcutaneous injection of kainic acid ("KA"; 10 mg/kg, Sigma). Because KA uptake is higher in young rats relative to adults (Berger et al., 1986, in Schwartz and Ben-Ari, *Advances in Experimental Medicine and Biology*, Plenum, N.Y., pp. 199-209), KA doses were adjusted to produce maximal excitotoxicity without reaching lethal doses (from 2 mg/kg at postnatal day P-7 to 6 mg/kg at postnatal day P25). Saline injected rats were used as controls (0 hour time point).

COX-1 and COX-2 cDNA Probes.

Bluescript plasmid (Stratagene) containing the full length rat COX-1 cDNA (2.7 kb) was linearized by digestion with ClaI; PCRII plasmid (Invitrogen) containing the coding sequence for rat COX-2 (1.8 kb) was linearized by digestion with PflMI (Feng et al., 1993, Arch. Biochem. Biophys. 307:361-368). Linearized plasmids were purified using Elu-Quick (Schleicher & Schuell) after agarose gel electrophoresis.

In Situ Hybridization.

At various intervals after the onset of KA-induced seizures, the rats were sacrificed, and the brains quickly removed, rinsed in cold phosphate buffer (PBS, 10 mM, pH 7.4) and immersed in methylbutane at −25° C. for three minutes. The brains were sliced into 10 micrometer sections, frozen, and the resulting frozen sections were mounted on polylysine-coated slides and stored at −70° C. For immunocytochemistry ("ICC") or in situ hybridization ("ISH"), frozen sections were post-fixed in PBS containing 4 percent paraformaldehyde (30 minutes at room temperature) and then rinsed in PBS. For ISH, tissue sections were rinsed in 0.1M triethanolamine ("TEA"), pH 8.0, incubated in acetic anhydride ("AAH"; 0.25% v/v in TEA, 10 minutes) and rinsed in TEA and PBS. Following AAH treatment, tissue sections were hybridized with [$^{35}$S]-cRNA probes (0.3 µg/ml, $2 \times 10^9$ dpm µg$^{-1}$) made from COX-2 linearized cDNA transcription vectors (Feng et al., 1993, Arch. Biochem. Biophys. 307:361-368). Sense strand hybridization was used as a control and gave negative results. Following hybridization for 3 hours at 50° C., stringent washes (0.1× SSC at 60° C.) and dehydration, slides were exposed to X-ray film for seven days for quantification. Slides were then exposed to NTB-2 emulsion (Kodak, Rochester, N.Y.) for microscopic analysis of COX-2 mRNA distribution. Following development, tissue sections were counterstained with cresyl violet. Film autoradiograms were analyzed quantitatively using an image analysis system with software from Drexel University (Tocco et al., 1992, Eur. J. Neurosci. 4:1093-1103). Statistics were calculated by ANOVA followed by additional posthoc analysis.

In Situ End Labeling.

In parallel studies, paraformaldehyde-fixed brain tissue sections were dehydrated, air dried and incubated with dATP, dCTP, dGTP (0.2 mM), dTTP (13 µM), digoxigenin-11-dUTP and DNA polymerase I (Boehringer Mannheim) at 10 units/100 µl at 37° C. for 2 hours. The reaction was stopped by addition of 20 mM EDTA, pH 8.0. Sections were incubated at room temperature overnight with an alkaline-phosphatase-conjugated digoxigenin antibody (Genius System, Boehringer Mannheim) diluted 1:200 in 5 percent sheep serum diluted in 150 mM NaCl, 100 mM TRIS-HCl, pH 7.5. Colorimetric detection with nitro blue tetrazolium and 5-bromo-4-chloro-3-indolyl-phosphate was performed with the Genius System by the manufacturer's protocol (Sakhi et al., Proc. Natl. Acad. Sci. U.S.A. 91:7525-7529).

Northern Blot Hybridization Assay.

RNA extraction was performed as follows. After sacrifice, rat brains were dissected and stored at −75° C. prior to processing. Total RNA was extracted from pools of hippocampal tissue (Pasinetti et al., 1994, J. Comp. Neurol. 339: 387-400). Briefly, tissues were homogenized for 1 minute in 4M guanidinium thiocyanate, 25 mM sodium citrate (pH 7.5), 0.5% sarcosyl and 0.1M β-mercaptoethanol, in a final volume of 0.5 ml. After acidified phenol/chloroform extraction and ethanol precipitation, the RNA pellet was rinsed consecutively with 70% and 100% ethanol. The purified RNA was then dissolved in 0.5% sodium dodecyl sulfate ("SDS") and stored at −75° C. Total RNA was quantified in a UV spectrophotometer. Total RNA (5 µg) from tissue was electrophoresed on denaturing (0.2M formaldehyde) agarose gels and transferred to a nylon membrane (Nylon 66 plus; Hoeffer, San Francisco Calif.) in 2×SSC. Blot hybridization was carried out with $10^6$ cpm/ml of antisense COX-1 or COX-2 [$^{32}$P]-cRNA probes in 50% formamide, 1.5× SSPE, 1% SDS, 0.5% dry milk, 100 µg/ml yeast total RNA and 500 mg/ml salmon sperm DNA at 53° C. for about 15 hours. Blots were washed to a final stringency of 0.2×SSC, 0.2% SDS at 72° C. Blots were exposed to Kodak X-ray film (XAR-5) with intensifying screens at −70° C.

Cell Cultures.

Hippocampal neuron cultures were derived from embryonic rat brain. E16-E18 embryos were dissected in Hank's balanced salt solution and cultured (Pasinetti et al., 1994, J. Comp. Neurol. 339:387-400; Peterson et al., 1989, Dev. Brain Res. 48:187-195). Culture media were changed every 3 days. For glutamate neurotoxicity studies, eight day old cultures were treated with glutamate (250 µM, Sigma) in the presence of 2.4 mM calcium ion and 0.8 mM magnesium ion. After 6 hours of glutamate exposure, culture medium was replaced with fresh medium; COX-2-like immunoreactivity was assessed in neurons 12 hours later.

Immunocytochemical Detection of COX-2 in Monotypic Cultures of Primary Rat Neurons.

Control and glutamate treated cultures were post-fixed in PBS containing 4% paraformaldehyde (30 minutes, room temperature), rinsed in PBS, pre-treated with normal serum and incubated overnight at 4° C. with primary antibodies. COX-2 antisera (rabbit IgG) was raised against a synthetic peptide (CNASASHSRLDDINPT; SEQ ID NO:1) encompassing the C-terminal region of the murine COX-2. The antisera reacts with human and rat COX-2 but not with COX-1, as assessed by Western blot analysis. Vectastain ABC kit (Vector, Burlingame, Calif.) was used in subsequent steps to complete the diaminobenzene staining Pasinetti et al., 1994, J. Comp. Neurol. 339:387-400). Immunoadsorption of COX-2 antisera with synthetic COX-2 peptides controlled for specificity; adsorption was carried out overnight at 4° C. with synthetic COX-2 peptides at 30 μg/ml.

6.2. Results

COX-2 Expression in Adult Rat Brain.

FIG. 1 shows by ISH that the regional distribution of COX-2 mRNA was most notable in limbic structures, but was also present in neocortex (consistent with the reports of Kaufmann et al., Proc. Natl. Acad. Sci. U.S.A. 93:2317-2321 and Yamagata et al., 1993, Neuron 11:371-386). In the hippocampal formation, COX-2 mRNA was selectively expressed in cells of the granule and pyramidal neuron layers. COX-2 mRNA expression was also found in the outer layer of the parietal cortex, the pyriform cortex and cells of the amygdaloid complex.

Maturational Regulation of Hippocampal COX-2 mRNA Expression.

ISH results indicated that during maturation, COX-2 mRNA expression is differentially regulated in subsets of cells of neuronal layers of the hippocampal formation (FIG. 2, FIG. 3 top). From postnatal days P7-P14, COX-2 mRNA showed greater than two-fold increase in the granule cell layer of the dentate gyrus and in the CA3 subdivision of the pyramidal cell layer ($p<0.001$, FIG. 2). Though the expression of COX-2 mRNA was lower in the other brain regions examined, the pattern of maturational expression was similar (FIG. 2). By postnatal day P21, COX-2 mRNA expression approximated adult levels in all subregions examined (FIG. 2, FIG. 3 top).

Response to KA-Induced Seizures.

Figure 4A:
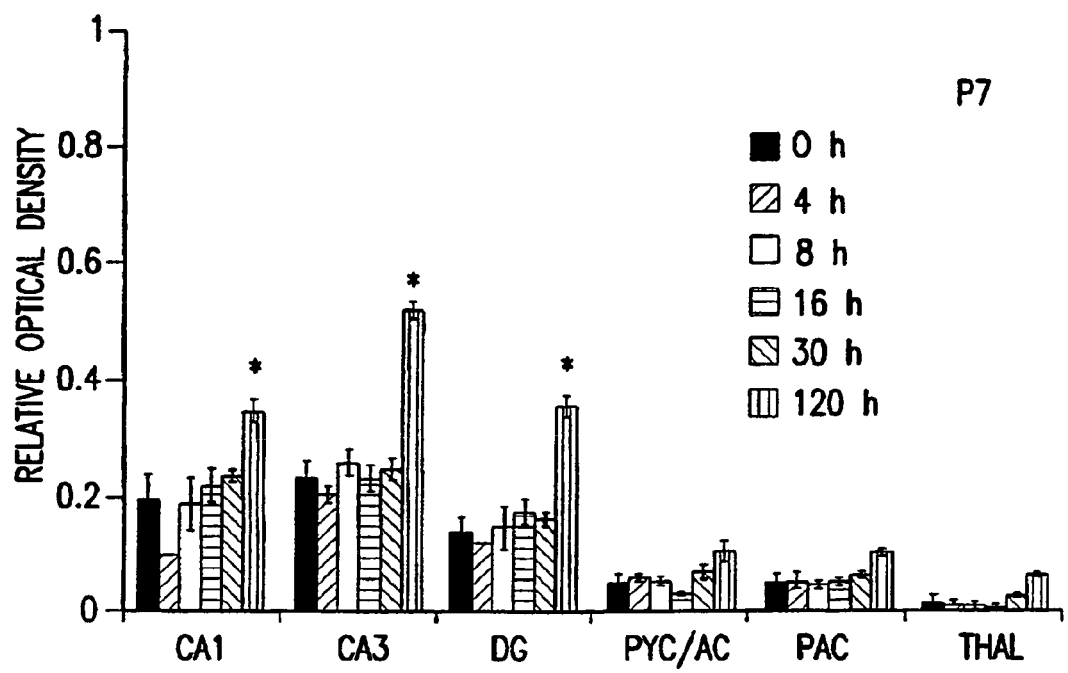
Figure 4B:
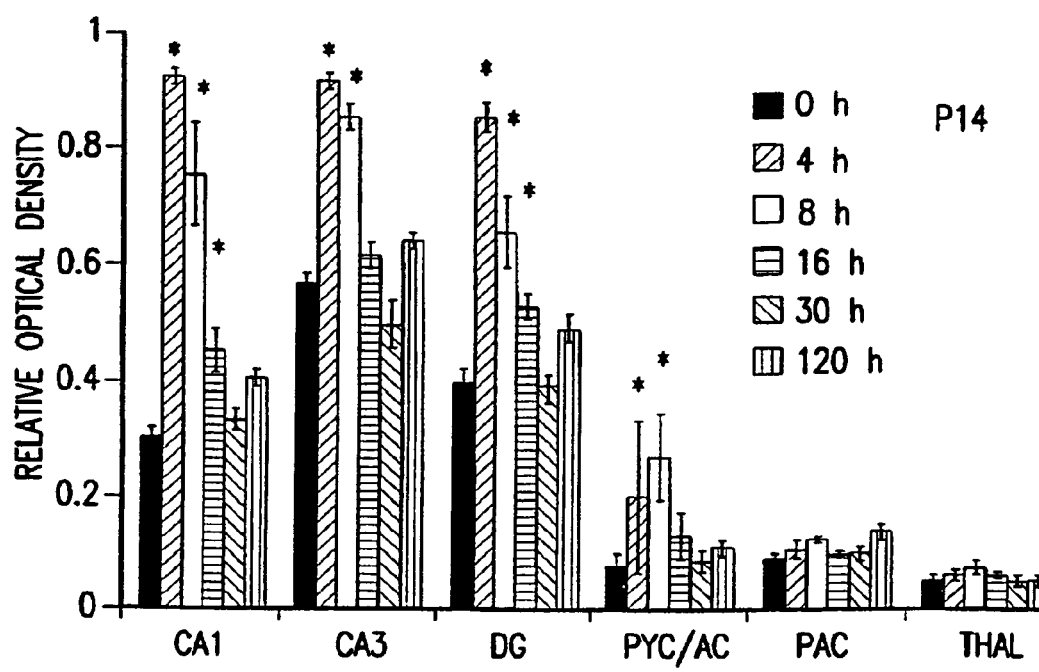
Figure 4C:
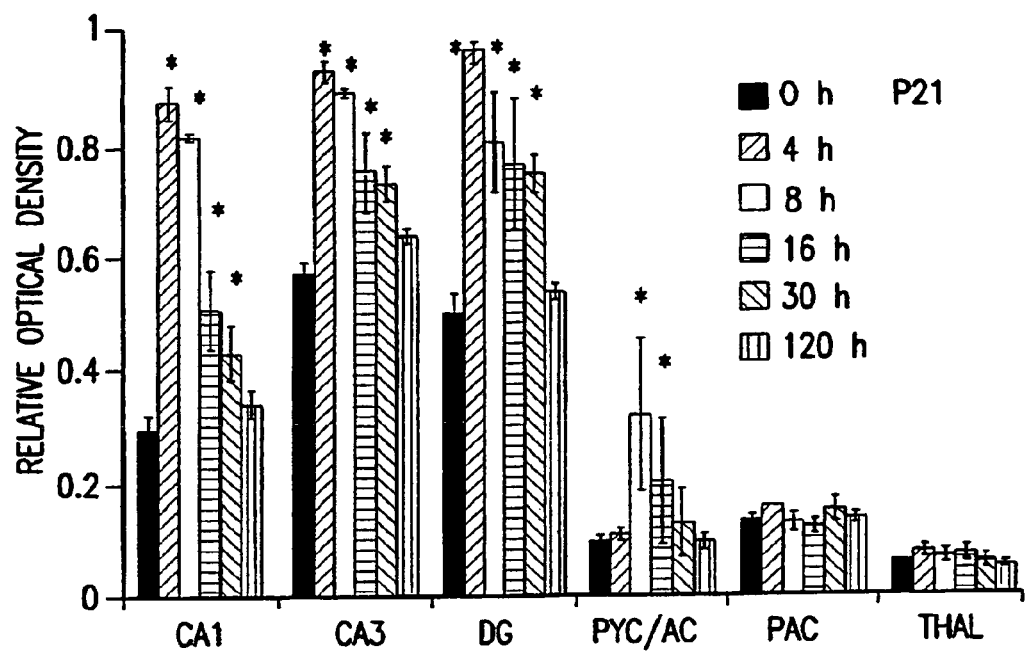
Figure 4D:
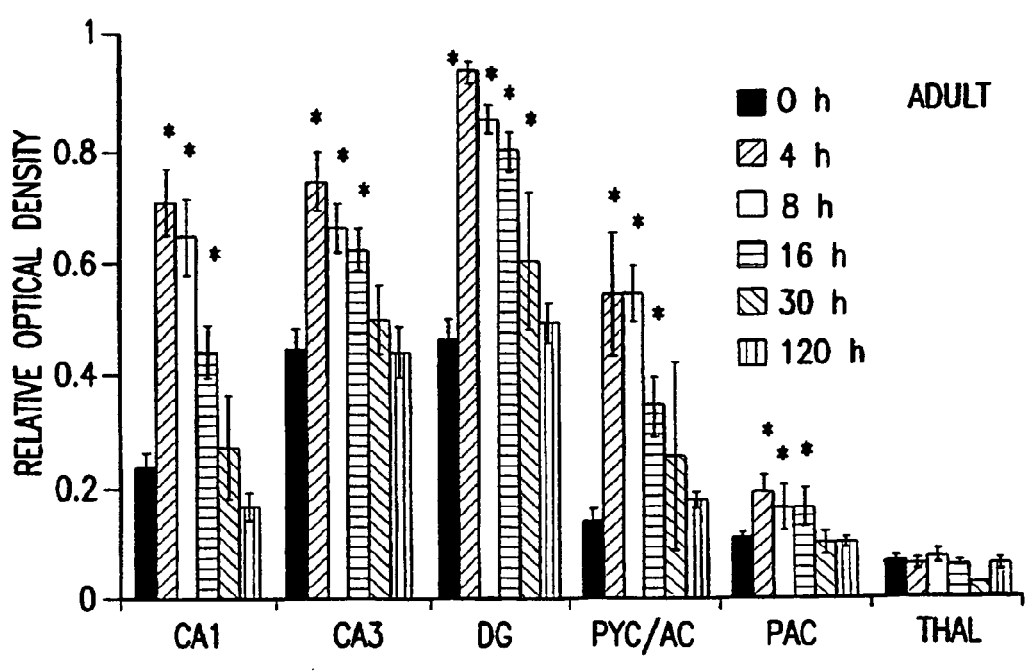

To further explore maturational regulation of COX-2 in brain, COX-2 mRNA expression during responses to KA-induced seizures was examined postnatally. Despite intense seizure activity after KA treatment, no detectable change of COX-2 mRNA expression was found in any brain region examined at P7 (FIG. 3, FIG. 4A). Changes in COX-2 mRNA expression at 120 hours post-KA treatment in the P7 group indicate developmental maturation rather than response to KA toxicity (FIG. 4A). In contrast to the P7 group, at P14 and P21 COX-2 mRNA increased within 4-8 hours after onset of KA-induced seizures in all the hippocampal subregions examined (FIGS. 4B and 4C). The level of COX-2 mRNA expression returned toward control levels within 120 hours after treatment in P14, P21 and adult rat brain.

Figure 5A:
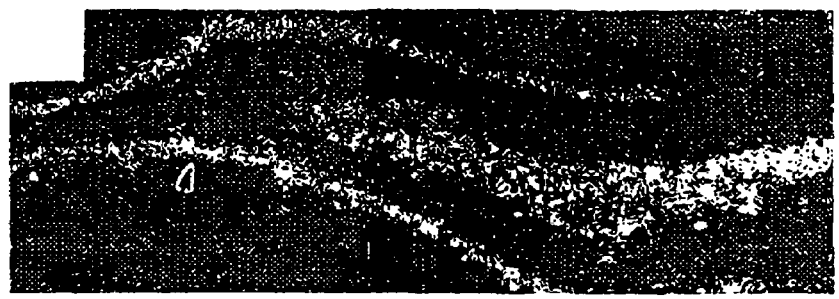
Figure 5B:
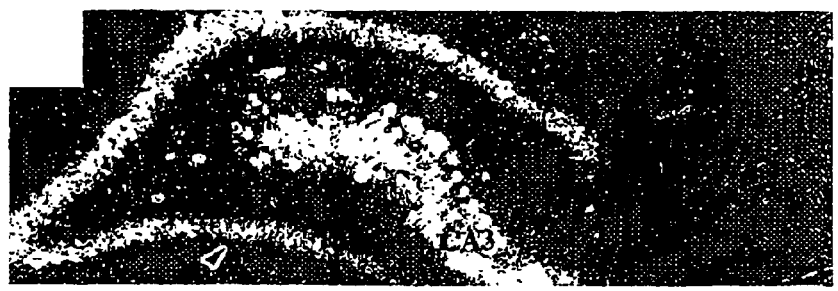
Figure 5C:
Figure 5D:

Within the dentate gyrus, control COX-2 expression in P14 and P21 rats was asymmetric, selectively localized to the more superficial neurons of the stratum granulosum rather than the deeper granule cells of the dentate gyrus blade (FIG. 5A). In response to KA treatment, COX-2 mRNA induction showed similar asymmetry of expression (FIG. 5B). In contrasts the asymmetry within the dentate gyrus was less notable in control animals and after KA-induction of the adult group (FIGS. 5C and 5D).

In parallel studies, northern blot hybridization of total RNA from hippocampus of adult rats 12 hours after KA-induced seizures confirmed COX-2 mRNA induction (FIG. 6). No detectable induction of COX-1 mRNA was found in the same rat brain (FIG. 6).

KA-Induced COX-2 and Apoptosis in Adult Rat.

By 8 hours after onset of KA-induced seizures, COX-2 mRNA induction in cells of the CA3 region of the hippocampal formation (FIG. 7B), pyriform cortex (FIG. 7E) and amygdaloid complex (FIG. 7H) of the adult brain paralleled temporally and overlapped anatomically the onset of apoptosis as assessed by in situ end-labeling in the same brain regions (FIG. 7C, CA3 regions of the hippocampus; FIG. 7F, pyriform cortex; FIG. 7I, amygdaloid complex). Cellular COX-2 mRNA expression in adult, control (FIGS. 7A, 7D and 7G) and KA-treated (FIGS. 7B, 7E and 7H) rats was identified by emulsion autoradiography using ISH assays.

Immunocytochemical Evidence of Neuronal COX-2 Expression/Regulation in Response to Glutamate in Vitro.

Primary cultures of rat hippocampal neurons were exposed to glutamate in vitro. At baseline, constitutive COX-2 expression was demonstrated by immunocytochemistry (FIG. 8B). Twelve hours after exposure to glutamate, an increase in COX-2 immunoreactivity was observed which coincided with marked reduction in the number of neurons (FIG. 8D).

COX-2 Expression in Human Epilepsy.

Increased expression of COX-2 mRNA was detected by ISH in a biopsy of human brain at epileptic foci (FIG. 17A-D). It was found that COX-2 mRNA, but not COX-1 mRNA, was significantly elevated in the cortex of epileptic patients. the p vlaue was $<0.05$.

7. EXAMPLE

Nimesulide Suppresses Cytokine and Nitrite Production in Microglia Cultures

Figure 9A:
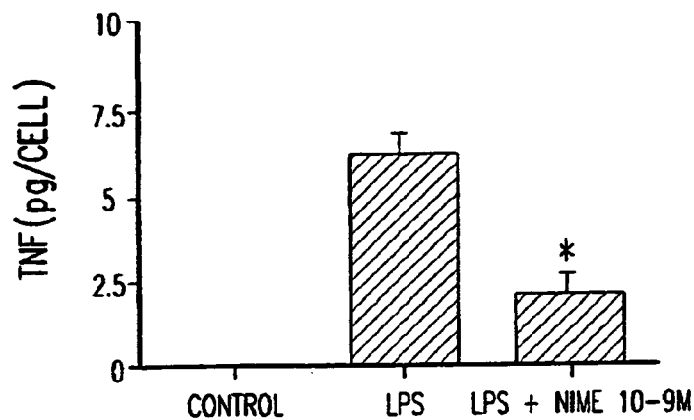
Figure 9B:
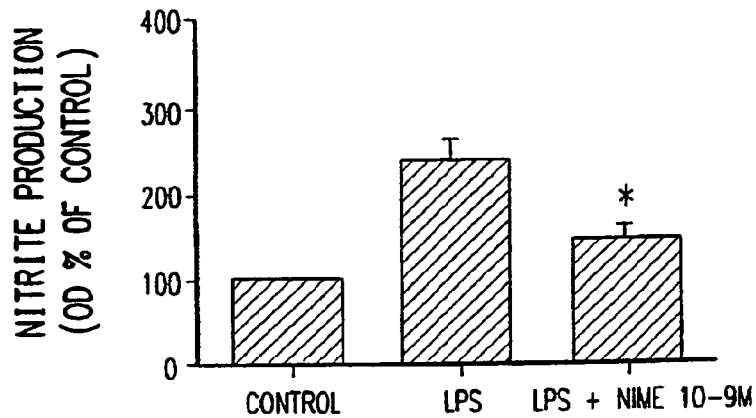
Figure 9C:
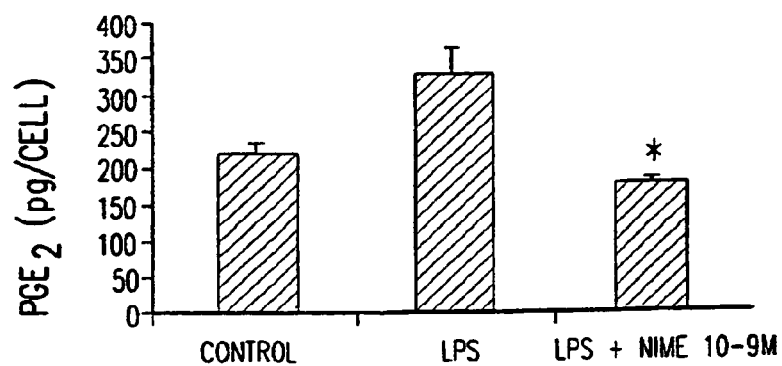
Figure 10A:
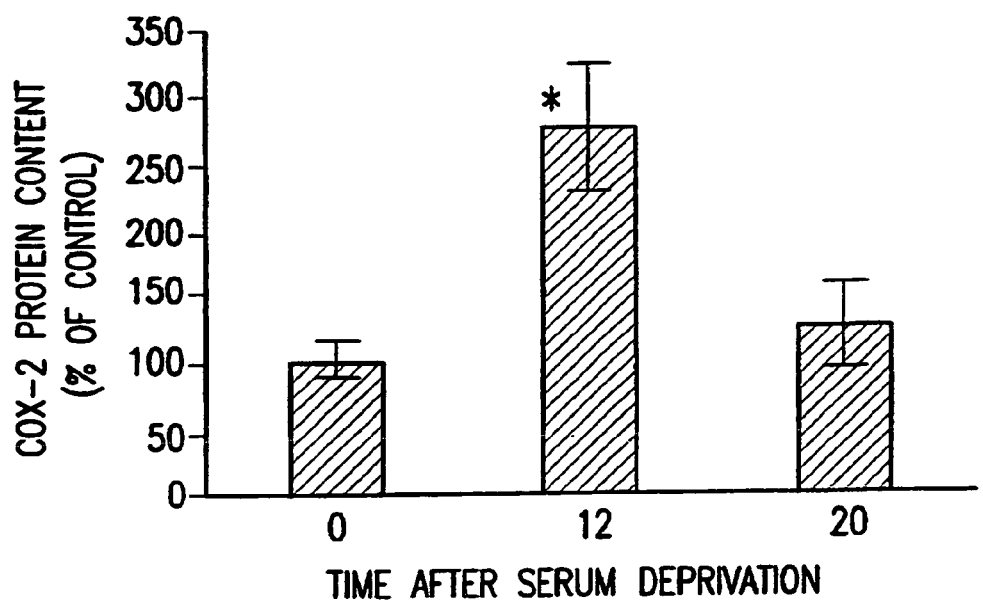
Figure 10C:
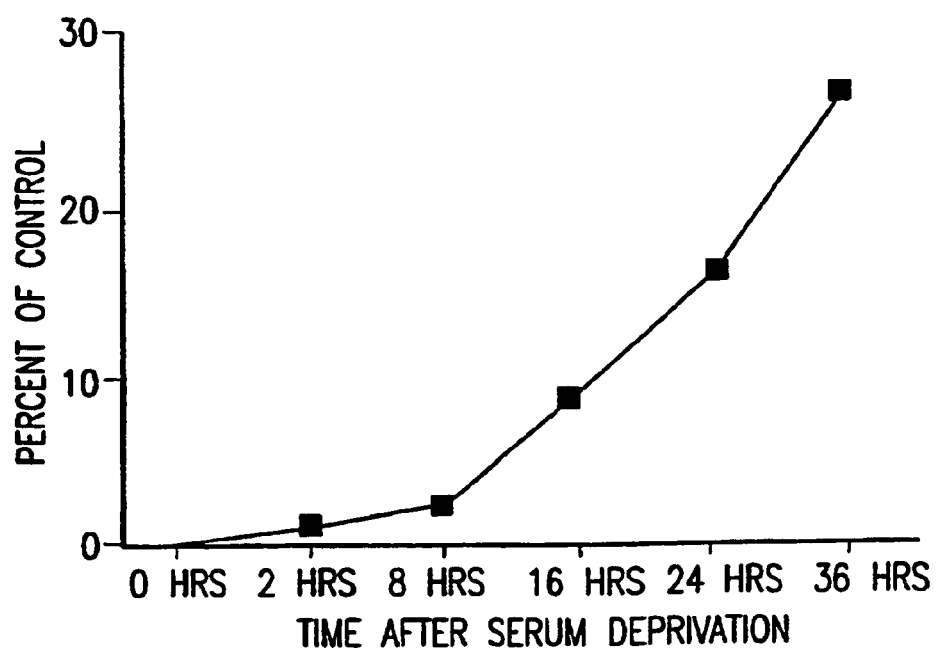
Figure 10E:
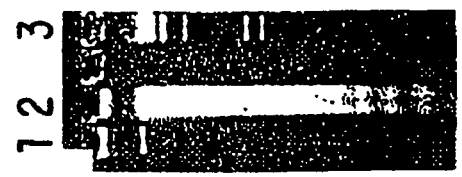
Figure 10D:
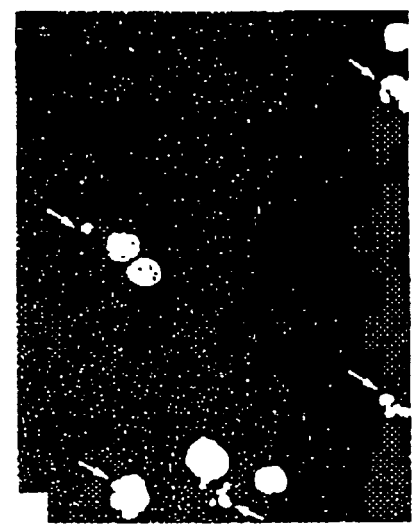
Figure 10B:
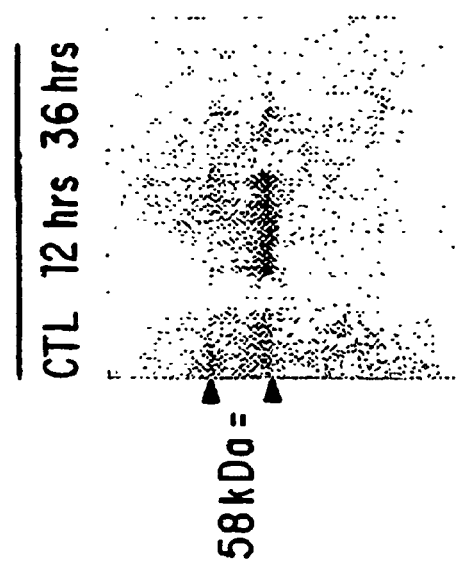

In experiments conducted in vitro, nimesulide at low concentration (1 nanomolar) was found to be effective in the suppression of endotoxin-mediated induction of tumor necrosis factor ("TNF") production by immortalized brain-derived microglia (BV-2) and astrocytes (FIG. 9A). In parallel, nimesulide was equally effective in blocking nitrite production (Griess reaction; FIG. 9B). This latter observation is particularly relevant in view of evidence showing that blockade of neuronal nitric oxide ("NO")-synthase protects against glutamate neurotoxicity. Nimesulide was also found to be effective in blocking endotoxin-mediated induction of prostaglandin $PGE_2$) in brain-derived microglia (FIG. 9C).

8. EXAMPLE

COX-2 Expression in Apoptotic Cells

The regulation of COX-2 expression was studied using an established in vitro model of apoptosis. Specifically, the regulation of COX-2 was studied in P19 embryonic carcinoma cells during responses to serum deprivation. Under such conditions, the P19 cells underwent apoptotic cell death, showing characteristic DNA fragmentation and nuclear morphology. As shown in FIG. 10, using this system coincidental onset of apoptosis and elevation of COX-2 expression was observed.

Figure 11A:
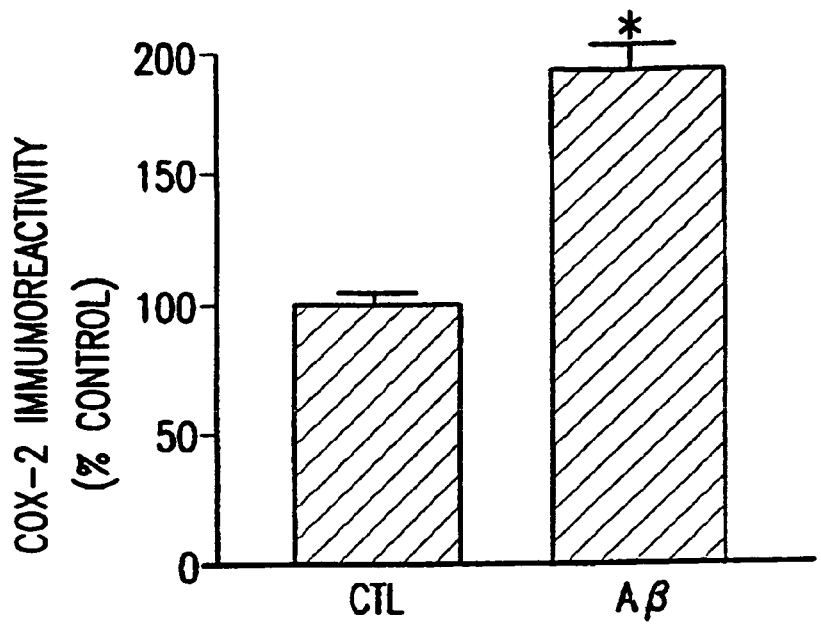
Figure 11C:
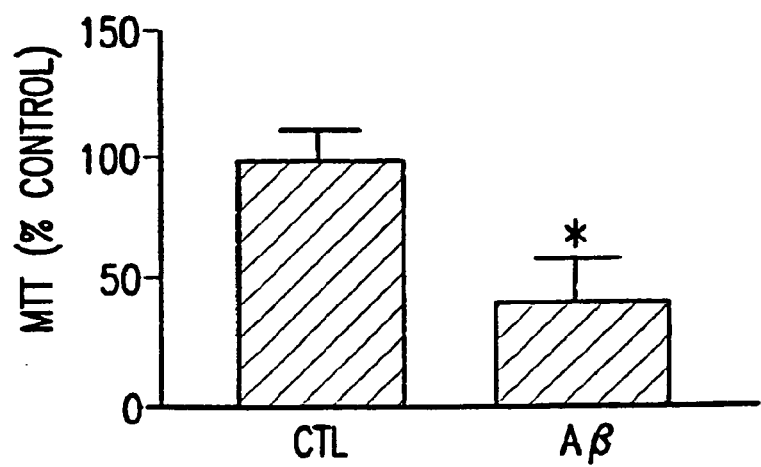
Figure 11E:
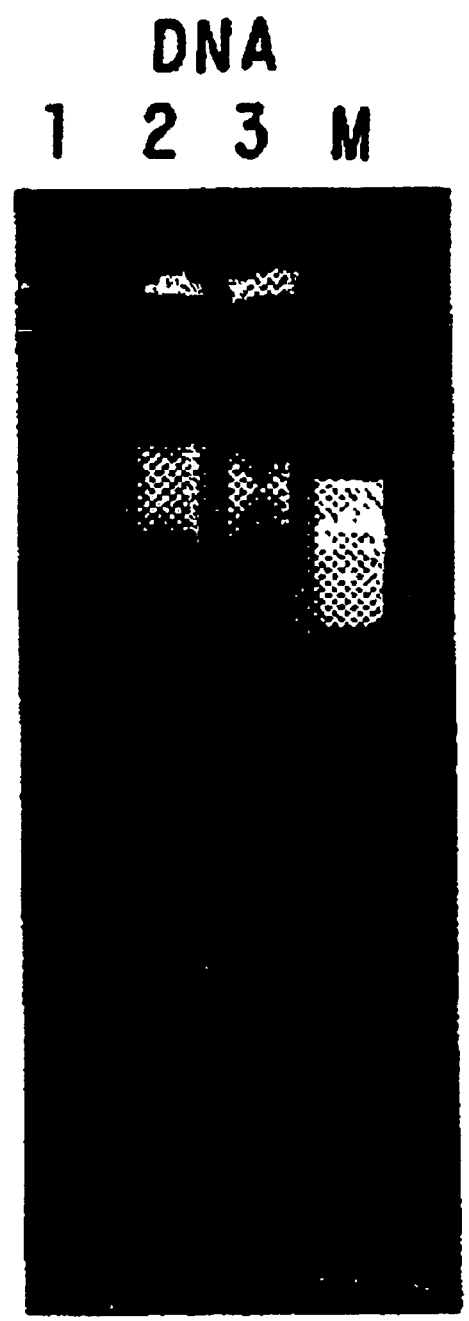

These studies were extended to the human neuronal cell line SH-SY5Y. β-amyloid has been demonstrated to play a role in inducing neurodegeneration in SH-SY5Y cells (Oda et al., 1995, Alzheimers Res. 1:29-34). SH-SY5Y cells were treated with synthetic aggregated $A\beta_{1-40}$ peptides at a concentration of 20 μM for various periods of time. Western blot analysis was performed of cell extracts, using COX-2 antisera or actin antisera as control (FIGS. 11B and D, respectively). In FIG. 11A, COX-2 protein from control or Aβ-treated SH-Sy5Y neuronal cells was quantified from the immunoblots shown in FIG. 11B (at the 72 hr. time point; only the 70 kDa mw species being quantified). COX-2 signal was abolished by immunoadsorption of COX-2 antisera with purified human recombinant COX-2 ("hrCOX-2") peptides. FIG. 11C shows that diminished cell redox activity was observed 72 hours after treatment with aggregated $A\beta_{1-40}$ (at 20 μm), as assessed by MTT assay in parallel cultures. Bar graphs represent the mean±SEM, n=4-5 per group, p<0.05 (t-test). COX-2 integrated optical densities were analyzed from digitized images using a Bioquant image analysis (Biometrics, Nashville, Tenn.). It was also found that COX-2 expression occurred in parallel to DNA laddering (FIG. 11E), an index of apoptosis. FIG. 12 shows that nimesulide at $10^{-6}$ and $10^{-9}$ molar was able to block Aβ1-40 toxicity, as assessed by the MTT assay.

Interestingly, when aggregated synthetic $A\beta_{1-40}$ peptides (150 μM) were coincubated with purified hr-holoCOX-2 (COX-2 plus heme-cofactor, 50 nM) for 16 hours, at 37° C. in 1×PBS, and cyclooxygenase and peroxidase activities were measured (Murphy et al., 1989, Neuron 2:1547-1558) cyclooxygenase and peroxidase activities increased (relative to activity levels of enzyme in the absence of Aβ; FIG. 18). Cyclooxygenase and peroxidase levels in the absence of heme gave negative results.

9. EXAMPLE

COX-2 Expression in Alzheimer's Disease

The expression of COX-2 in normal human brains and in brains of Alzheimer's Disease ("AD") patients was studied. Immunochemical data indicates that COX-2 expression is primarily localized to cells with neuronal morphology in human brain; minimal localization of COX-2 immunostaining in cells with glial morphology was found in any region examined. These results tend to suggest a role for COX-2 in a non-inflammatory function. While the immunocytochemical signal for COX-2 was at the limit of detection in temporal cortex of neurological control cases, COX-2 showed elevation in AD brain (FIG. 13A, 13B) The selective induction of COX-2 immunoreactivity in grey matter is consistent with the findings showing neuronal induction of COX-2 in rat brain during responses to lesions leading to neuronal death (see Section 6).

The cellular immunodistribution of COX-2 in AD brain was also explored. It was observed that neuronal COX-2 is not only localized to the perikarya (FIG. 14A, but is found in neuronal projections as well (FIG. 14B). Moreover, intense immunostaining was also found in diffuse plaques (FIG. 14C) and in AD neuritic plaques identified by Aβ immunostaining on adjacent tissue sections of the hippocampal formation. These findings suggest a role for COX-2 in mechanisms of neuronal death or survival.

Studies were performed to quantify COX-2 expression in brains of AD and age-matched controls. We used quantitative dot-blot analysis and chemiluminescence detection. Western analysis was used for qualitative assessment. A greater than 2-fold elevation of COX-2 content was found in hippocampal homogenates of AD brains compared to neurological age-matched controls.

Because of the immunocytochemical evidence showing COX-2 immunoreactivity in AD plaques, levels of COX-2 and total Aβ in AD cases were compared. A direct correlation was found.

Figure 15B:
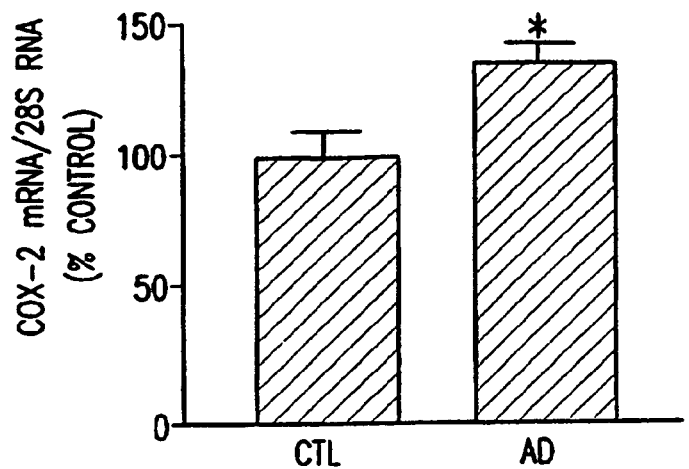

COX-2 mRNA and protein were found to be increased in AD brain frontal cortex. FIG. 15A shows Northern blots of total RNA from neurological control (C) and AD frontal cortex hybridized to [$^{32}$P] COX-2 and COX-1 mRNAs. The mRNA species detected by COX-2 and COX-1 cRNA probes represent an RNA of the same size found in peripheral tissues. FIG. 15B shows quantified results of the Northern studies. Specifically, COX-2 mRNA prevalence was increased in the frontal cortex of AD vs control, where the presence of equal amounts of RNA in both lanes was confirmed by normalization to 28S rRNA in the hybridization membrane, and complete transfer of RNA to the membrane was evidenced by the absence of 28S and 18S rRNAs in the gel post transfer. Integrated optical densities were analyzed from digitized images using a Biquant image analysis. Bar graphs represent n=9 per group, and the results were significant by a t-test value of p<0.05.

Figure 15D:
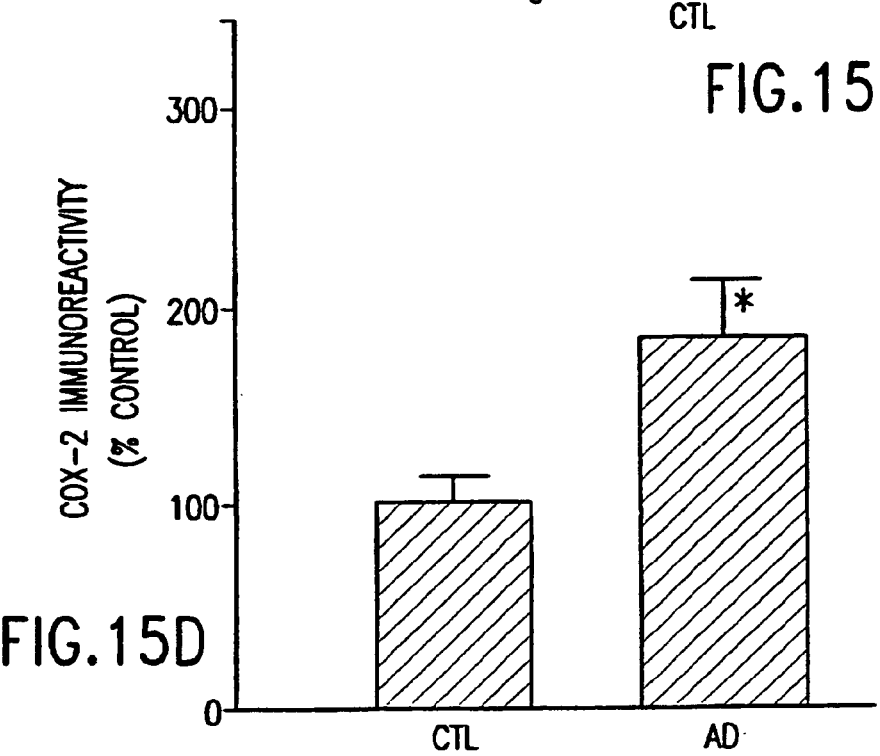
Figure 15E:
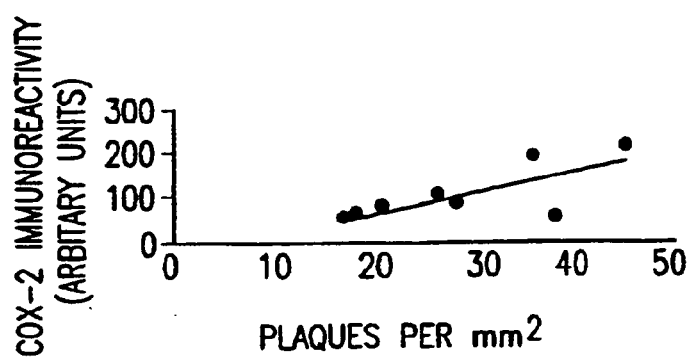
Figure 15C:
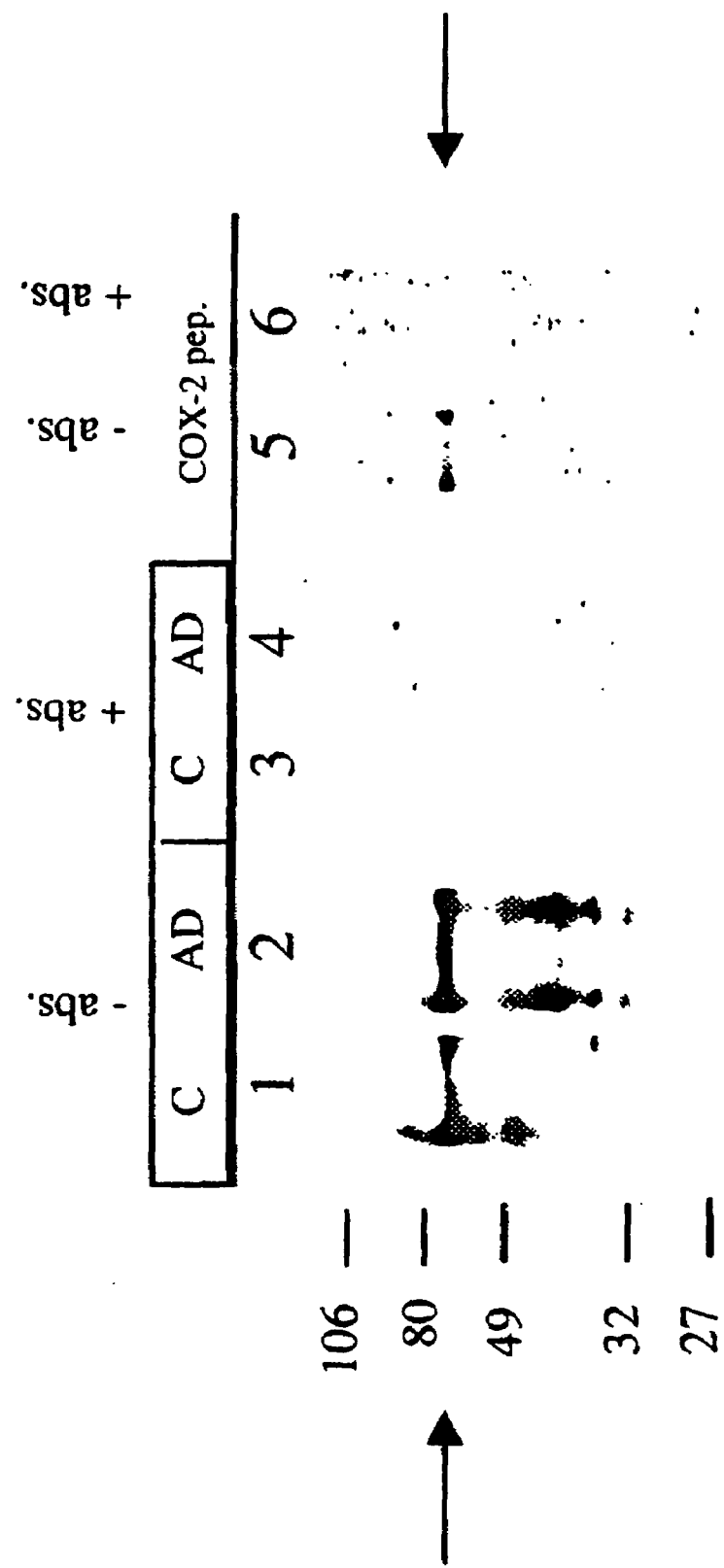

Similarly, when Western blot analysis was performed of AD frontal cortex vs. controls, the amount of COX-2 protein was found to increase. FIG. 15C shows the results of such a western blot. Lanes 1 and 2 show the COX-2 protein content of the same tissues uses for Northern analysis. Lanes 3-4 show the absence of COX-2 bound when COX-2 antisera was immunoadsorbed using hrCOX-2 peptides, demonstrating the specificity of the signal.

The expected 70 kDa new species of hrCOX-2 (lane 5) also was absent when antisera was preadsorbed with hr COX-2 peptides. These results are quantified in FIG. 15D (with respect to the 70 kDa species). Further, the immunoblots were stripped and immunoreacted with actin antisera to verify the specificity of changes (actin values: control group 100±8; AD 94±70% of control Bar graphs represent n=9 per group; t-test value is p<0.05). The inset in FIG. 15D shows a correlation of COX-2 content and the number of plaques per mm$^2$, n=8, r=0.72, p<0.03. COX-2 and actin integrated optical densities were analyzed from digititzed images using Biquant image analysis.

10. EXAMPLE

COX-2 Expression in Amyotrophic Lateral Sclerosis

In situ hybridization has demonstrated increased COX-2 mRNA in the anterior horn cells of spinal cords of patients suffering from amyotrophic lateral sclerosis ("ACS"); FIG. 16.

11. EXAMPLE

Transient Expression of COX-2 in Neuronal Cells Aβ Mediated Impairment of Redox Activity Potentiates The role of COX-2 in neuronal death and/or survival was studied in cultured human SH-SY5Y neuronal cells. Cells were transiently transfected with a mammalian expression vector (pRc/CMV/hCOX, Invitrogen) containing either a full length human (h) COX-2 cDNA (pRc/CMV/hCOX-2), or a bacterial chloramphenicol acetyltransferase (CAT) gene (pRc/CMV2/CAT). Following Aβ25-35 treatment, impairment of redox activity as assessed by 3-(4,5-dimethylthiazol-2-yl)-2,5-diphenyltetraxolium bromide (MTT)-assay (FIG. 19). Overexpression of hCOX2 in SH-SY5Y cells transfected with pRc/CMV/hCOX-2 was confirmed immunocytochemically in a parallel tissue culture chamber slide using an α-COX-2 antibody as previously described. In control cells transfected with pRc/CMV2/CAT, the same α-COX antibody generated minimal immunocytochemical signal. We found that transient overexpression of hCOX-2 in SH-SY5Y neuronal cells potentiated Aβ25-35 (25 µM, 48 hrs treatment) mediated impairment of redox activity when compared to SH-SY5Y cultures transfected with control vector (±±p<0.01 vs Aβ/control vector, *p<0.001 vs CTL. These data are consistent with evidence showing induction of COX-2 mRNA coincidentally with impairment of redox activity in SH-SY5Y neuronal cells (FIG. 11).

12. EXAMPLE

Experiments Using COX-2 Transgenic Mice

Based on the evidence that overexpression of COX-2 in neuronal cells may potentiate Aβ-mediated redox impairment and the observation that neuronal COX-2 is elevated in AD brain and in experimental neurodegeneration, we generated a transgenic mouse model with neuronal overexpression of human (h) COX-2. To obtain overexpression of hCOX-2 in neurons, a hybrid gene was prepared in which the expression of a cDNA sequence containing the entire hCOX-2 coding region is regulated by the rat neuron-specific enolase (NSE) promoter.

We obtained four lines with high expression of hCOX-2 mRNA expression. In one of them (NHC32), COX-2 mRNA was assessed by in situ hybridization analysis (FIG. 20A). We found that in NHC32 mouse line, has high levels of hCOX-2 mRNA in the hippocampal formation, cerebral cortex and in other neuronal layers (FIG. 20B). No white matter level of HCOX-2 mRNA were found using combined immunocytochemistry for NSE and hCOX-2 in situ hybridization on the same tissue section, we confirmed the selectivity of hCOX-2 transgene expression to neuronal cells.

It has further been shown, using neuronal cultures derived from the transgenic mice, that hCOX-2 overexpression potentiated Aβ mediated response. As depicted in FIG. 21, studies showed that primary neuronal cultures derived from transgenic mice with neuronal COX-2 overexpression (NHC32, n=3), are most susceptible to aggregated Aβ25-35 peptides mediated impairment of redox activity (MTT assay, Aβ25-35 25 µM for 48 hrs), when compared to equally treated neuronal cultures derived from wild type/control littermates (n=4). Moreover, when examined morphologically, Aβ25-35 treated neurons derived from transgenic hCOX-2 mice revealed an intensified regression of neuronal processes (B, inset) when compared to wild type control Aβ25-35 treated neuronal cultures (A, inset).

13. EXAMPLE

Nimesulide Protects B132 Neuronal Cells Against Glutamate Toxicity

We examined the role of nimesulide, indomethacin and NS398 (another COX-2 preferential inhibitor) on glutamate mediated toxicity. In this study we used B12 neuronal cells; toxicity was assessed by amount increase of lactate dehydrogenase LDH levels in the conditioned medium after treatment. LDH is an index of cell toxicity and its elevation is generally accepted as marker of neurotoxicity. As shown in FIGS. 22-23, we found that nimesulide protected against glutamate toxicity (10 mM) at 10-6, 10-9 and 10-12 M with pretreatment (24 hrs before) and cotreatment (with glutamate for 24 hrs). Indomethacin, protected at 10-6 M and lost its protective effect at 10-9 and 10-12 M. Marginal protection of glutamate mediated toxicity by indomethacin was observed at 10-9 M (pretreatment 24 hrs). No protection was observed with NS398 pretreatment. In the pretreatment condition drugs remained in the media during glutamate treatment.

Various publications are cited herein, the contents of which are hereby incorporated in their entireties.

---

---

What is claimed is:

1. A method of providing a neuroprotective effect against β-amyloid toxicity comprising administering, to a population of neurons, an effective amount of nimesulide.

2. The method of claim 1, wherein the amount of nimesulide administered decreases neuronal cell death by at least 20 percent.

3. The method of claim 1, wherein the neurons are exposed to a concentration of nimesulide of at least 1 picomolar.

* * * * *

UNITED STATES PATENT AND TRADEMARK OFFICE
CERTIFICATE OF CORRECTION

PATENT NO.        : 7,226,948 B2
APPLICATION NO. : 10/150461
DATED             : June 5, 2007
INVENTOR(S)       : Giulio M. Pasinetti and Paul S. Aisen It is certified that error appears in the above-identified patent and that said Letters Patent is hereby corrected as shown below:

IN THE SPECIFICATION:
Please insert, before Col. 1, line 17 ("INTRODUCTION"), the following paragraph:

-- This invention was made with government support under NIA grant numbers AG 13799, AG 14239, AG 05138, and AG 14766 awarded by the National Institutes on Aging. The United States Government has certain rights in the invention. --

Signed and Sealed this

Twenty-seventh Day of October, 2009

David J. Kappos
*Director of the United States Patent and Trademark Office*

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: synthetic peptide

<400> SEQUENCE: 1

Cys Asn Ala Ser Ala Ser His Ser Arg Leu Asp Asp Ile Asn Pro Thr
 1               5                  10                  15